US007635580B2

(12) United States Patent
Schröder et al.

(10) Patent No.: US 7,635,580 B2
(45) Date of Patent: Dec. 22, 2009

(54) METHOD FOR THE PRODUCTION OF SULPHER-CONTAINING FINE CHEMICALS BY FERMENTATION

(75) Inventors: Hartwig Schröder, Nußloch (DE); Burkhard Kröger, Limburgerhof (DE); Oskar Zelder, Speyer (DE); Corinna Klopprogge, Mannheim (DE); Stefan Häfner, Ludwigshafen (DE)

(73) Assignee: Evonik Degussa GmbH, Essen (DE)

( * ) Notice: Subject to any disclaimer, the term of this patent is extended or adjusted under 35 U.S.C. 154(b) by 911 days.

(21) Appl. No.: 10/514,489

(22) PCT Filed: May 23, 2003

(86) PCT No.: PCT/EP03/05423

§ 371 (c)(1),
(2), (4) Date: Nov. 15, 2004

(87) PCT Pub. No.: WO03/100072

PCT Pub. Date: Dec. 4, 2003

(65) Prior Publication Data

US 2008/0118959 A1 May 22, 2008

(30) Foreign Application Priority Data

May 23, 2002 (DE) ................. 102 22 858

(51) Int. Cl.
*C12P 13/12* (2006.01)
*C12P 21/06* (2006.01)
*C12N 9/10* (2006.01)
*C12N 1/20* (2006.01)
*C12N 15/70* (2006.01)
*C12Q 1/48* (2006.01)
*C07H 21/04* (2006.01)

(52) U.S. Cl. ............... 435/113; 435/252.3; 435/193; 435/320.1; 435/69.1; 435/15; 536/23.2

(58) Field of Classification Search ............ None
See application file for complete search history.

(56) References Cited

U.S. PATENT DOCUMENTS

| 4,489,160 | A | 12/1984 | Katsumata et al. |
| 4,601,893 | A | 7/1986 | Cardinal et al. |
| 5,158,891 | A | 10/1992 | Takeda et al. |
| 5,175,108 | A | 12/1992 | Bachmann et al. |
| 5,811,238 | A | 9/1998 | Stemmer et al. |
| 5,965,391 | A | 10/1999 | Reimscheid et al. |
| 6,821,758 | B1 | 11/2004 | Koltermann et al. |
| 2003/0092026 | A1* | 5/2003 | Rey et al. ............ 435/6 |
| 2003/0170775 | A1 | 9/2003 | Pompejus et al. |

FOREIGN PATENT DOCUMENTS

| EP | 11 08 790 | 6/2001 |
| JP | 07 227 287 A | 8/1995 |
| JP | A-1 0-229891 | 9/1998 |
| WO | WO 01/00843 A2 | 1/2001 |
| WO | WO 02/10209 A1 | 2/2002 |
| WO | WO 03/023044 A2 | 3/2003 |

OTHER PUBLICATIONS

Reczkowski R.S. et al. Structural and functional roles of cysteine 90 and cysteine 240 in S-adenoseylmethionine synthetase. The Journal of Biological Chemistry, vol. 270, No. 31, Aug. 4, 1995, pp. 18484-18490, XP002260183.

Database WPI, Section Ch, Week 200103, Derwent Publications Ltd., London, GB; Class B05, AN 2001-018703, XP002260186 & JP 2000 139471.

Nakamori S. et al. "Mechanism of L-methionine overproduction by *Escherichia coli*: The replacement of Ser-54 by Asn in the MetJ protein causes the derepression of L-methionine biosynthetic enzymes", Applied Microbiology and Biotechnology, vol. 52, No. 2, Aug. 1999, pp. 179-185, XP002242975.

Shen Bo et al "High free-methionine and decreased lignin content result from a mutation in the Arabidopsis S-adenosyl-L-methionjne synthetase 3 gene." The Plant Journal: For Cell and Molecular Biology, vol. 29, No. 3, Feb. 2002, pp. 371-380, XP002260184.

Goto D B et al. "A single-nucleotide mutation in a gene encoding Sadenosylmethionine synthetase is associated with methionine over-accumulation phenotype in *Arabidopsis thaliana*" Genes and Genetic Systems, vol. 77, No. 2, Apr. 2002, pp. 89-95, XP002242977.

Grossmann K et al. "Rapid cloning of *metK* encoding methionine adenosyltransferase from *Corynebacterium glutamicum* by screening a genomic library on a high density colony-array", FEMS Microbiology Letters, vol. 193, No. 1, Dec. 1, 2000, pp. 99-103, XP000984551.

Sekowska a. et al. "Sulfur metabolism in *Escherichia coli* and related bacteria: Facts and fiction", Journal of Molecular Microbiology and Biotechnology, vol. 2, No. 2, Apr. 2000, pp. 145-177, XP002242976.

Wei Yuhong et al. "Studies on the role of the *metK* gene product of *Escherichia coli* K-12.", Molecular Microbiology, vol. 43, No. 6, Mar. 2002, pp. 1651-1656, XP002260185.

Weissbach. H. et al. (1991) Mol Microbiol. 5 (7), 1593-1597.
Wel, Y. (2002) Mol. Microbiol. 43 (6), 1651-1656.
Markham, G.D. et al. (1983) Methods in Enzymology vol. 94, 219-222.
Sahm H. et al. Biological Chemistry 381(9-10):899-910, 2000.
Eikmanns B.J. et al. 64:145-63, 1993-94.

(Continued)

Primary Examiner—Richard Hutson
Assistant Examiner—Iqbal H Chowdhury
(74) Attorney, Agent, or Firm—Novak Druce & Quigg LLP

(57) ABSTRACT

The invention relates to methods for the production of sulfur-containing fine chemicals, in particular L-methionine, by fermentation using bacteria in which a nucleotide sequence encoding an S-adenosylmethionine synthase (metK) gene is expressed.

8 Claims, 1 Drawing Sheet

OTHER PUBLICATIONS

William R. Pearson et al. Proc. Natl. Acad. Sci. (USA) 85(8), 1988, 2444-2448.

Narang, S.A. (1983) Tetrahedron 39:3—DNA Synthesis.

Itakura et al. (1984) Annual. Rev. Biochem. 53:323, "Synthesis and use of Synthetic Oligonucleotides".

Itakura et al. (1984) Science 198:1056—"Expression in *Escherichia coli* of a Chemically Synthesized Gene for the Hormone Somatostatin".

Ike et al. (1983) Nucleic Acids Res. 11:477, "Solid phase synthesis of polynucleotides. VIII. Synthesis of mixed oligodeoxyribonucleodites by the phosphortriester solid phase method".

Coco et al. 2001: "DNA shuffling method for generating highly recombined genes and evolved enzymes", Nature Biotechnol. 19:354-359.

Leung et al. (1989): "A method for random mutagenesis of a defined DNA segment using a modified polymerase chain reaction", Technique 1:11-15.

Willem P.C. Stemmer (1994): „DNA shuffling by random fragmentation and reassembly: in vitro recombination for molecular evolution, Proc. Natl. Acad. Sci USA, 91:10747-10751.

Arkin et al. (1992) PNAS 89:7811-7815, "An algorithm for protein engenineering: Simulations of recursive ensemble mutagenesis".

Delagrave et al. (1993) Protein Engineering 6(3) :327-331, "Recursive ensemble mutagenesis".

Kohara et al. Cell 50, 495-508, "The Physical Map of the Whole *E. coli* Chromosome: Application of a new Strategy for Rapid Analysis and Sorting of a Large Genomic Library.", 1987.

Wahl et al. (1987) Proceedings of the National Academy of Sciences USA, 84: 2160-2164, "Cosmid vectors for rapid genomic walking, restriction mapping, and gene transfer".

Francisco Bolivar Life Sciences, 25, 807-818 (1979), "Minireview—Molecular Cloning Vectors Derived from the CoLE1 Type Plasmid pMB1".

Vieira et al. 1982, Gene, 19: 259-268, "The pUC plasmids, an M13mp7-derived system for insertion mutagenesis and sequencing with synthetic universal primers".

Grant et al. Proceedings of the National Academy of Sciences USA 87 (1990) 4645-4649, "Differential plasmid rescue from transgenic mouse DNAs into *Escherichia coli* methylation-restriction mutants".

Sanger et al. Proceedings of the National Academy of Sciences of the United States of America, 74: 5463-5467, 1977, "DNA sequencing with chain-terminating inhibitors".

Roger Staden Nucleic Acids Research (1986) 14, 217-232, "The current status and portability of our sequence handling software".

Christian Marck Nucleic Acids Research (1988) 16, 1829-1836, "'DNAStrider': a 'C' program for the fast analysis of DNA and protein sequences on the Apple Macintosh family of computers".

B. A. Butler Methods of Biochemical Analysis (1998) 39, 74-97, "Sequence Analysis Using GCG".

Liebl et al. International Journal of Systematic Bacteriology (1991)41:255-260, "Transfer of *Brevibacterium divaricatum* DSM 20297, '*Brevibacterium flavum*' DSM 20411, . . . Gene Restriction Patterns".

Ben-Bassat et al. (1987) Journal of Bacteriology 169: 751-757, "Processing the Initiation Methionine from Proteins: Properties of the *Escherichia coli* Methionine Aminopeptidase and Its Gene Structure".

O'Regan et al. (1989) Gene 77: 237-251, Cloning and nucleotide sequence of the phosphoenolpyruvate carboxylase-coding gene of *Corynebacterium glutamicum* ATCC13032.

Sahin-Toth et al. (1994) Protein Sciences 3: 240-247, Cysteine scanning mutagenesis of the N-Terminal 32 amino acid residues in the lactose permease of *Escherichia coli*.

Hochuli et al. (1988) Biotechnology 6: 1321-1325, "Genetic Approach to Facilitate Purification of Recombinat Proteins with a Novel Metal Chelate Adsorbent".

Motoyama, H. et al. Applied & Environmental Microbiology. 67:3064-70, 2001, "Overproduction of L-Lysine Methanol by . . . with a Mutated *dapA* Gene".

B. Eikmanns. (1992) Journal of Bacteriology 174: 6076-6086, "Identification, Sequence Analysis, and Expression . . . Triosephosphate".

Martin et al. Biotechnology 5, 137-146 (1987), "Cloning Systems in Amino Acid-Producing Corynebacteria".

Guerro et al. Gene 138, 35-41 (1994), Directed mutagenesis of a regulatory . . . operon.

Tsuchiya et al. Bio/Technology 6, 428-430 (1988), Genetic Control Systems of . . . in Coryneform Bacteria.

Eikmanns et al. Gene 102, 93-98 (1991). "A family of . . . , and promoter probing".

Schwarzer et al. Biotechnology 9, 84-87 (1991), "Manipulation of . . . and Replacement".

Reinscheid et al. Applied and Environmental Microbiology 60, 126-132 (1994), "Stable Expression of . . . and Related Amino Acids".

LaBarre et al. (Journal of Bacteriology 175, 1001-1007 (1993). "Gene Replacement, Integration, and Amplification. . . . *glutamicum*".

Malumbres et al Gene 134, 15-24 (1993), "Codon preference in Corynebacteria".

Jensen et al. Biotechnology and Bioengineering 58, 191-195 (1998), "Artificial Promoters for Metabolic Optimization".

Makrides, Savvas Microbiological Review 60:512-538 (1996), "Strategies for Achieving High-Level Expression of Genes in *Escheria coli*. . .".

Patek et al. Microbiology. 142, 1297-309, 1996, "Promoters from. . . . consensus motif".

Sonnen et al. Gene 107: 69-74 (1991), Characterization of . . . , a new plasmid from *Corynebacterium glutamicum* LP-6.

Serwold-Davis et al. FEMS Microbiology Letters 66, 119-124 (1990), "Localization of an origin of replication in . . . *Escherichia coli*".

Simon et al. Bio/Technology 1, 784-791 (1983), "A broad Host Range . . . Gram Negative Bacteria".

Schaefer et al. Gene 145, 69-73 (1994), "Small mobilizable multipurpose cloning vectors .derived from the . . . *Corynebacterium glutamicum*".

Bernard et al. Journal of Molecular Biology, 234: 534-541 (1993), "The F Plasmid CcdB Protein Induces Efficient ATP-dependent DNA Cleavage by Gyrase".

Schrumpf et al. 1991, Journal of Bacteriology 173: 4510-4516, "A functionally Split Pathway for Lysine. . . . *Corynebacterium glutamicum*".

Spratt et al. 1986, Gene 41, 337-342, "Kanamycin-resistant vectors that are analogoues of plasmids . . . pEMBL9".

Thierbach et al. Applied Microbiology and Biotechology 29, 356-362 (1988), "Transformation of spheroplasts and protoplasts of *Corynebacterium glutamicum*".

Dunican et al. Biotechnology 7, 1067-1070 (1989), "High Frequency Transformation of Whole Cells of Amino . . . Voltage Electroporation".

Tauch et al. FEMS Microbiological Letters 123, 343-347(1 994), "*Corynebacterium glutamicum* DNA is subjected to methylation-restriction in *Escheria coli*".

Patek et al. (1994) Appl. Environ. Microbiol. 60 :133-140, "Leucine Synthesis in *Corynebacterium glutamicum*. . . Inactivation on Lysine Synthesis".

Malakhova et al. (1996) Biotekhnologiya 11 27-32, "Thin-Layer Chromatography of free amino acid. Selection of Conditions. . . , and L-Thereonine".

Schmidt et al. (1998) Bioprocess Engineer. 19 :67-70, "Near infrared spectroscopy in fermentation and quality control for amino acid production".

Lennox, E. S. 1955, Virology, 1:190-206, "Transduction of Linked Genetic Characters of the Host by Bacteriophage P1".

Tauch et al. (1995) Plasmid 33: 168-1 79, "The Erythromycin Resistance . . . Is Capable of Transposition in *Corynebacterium glutamicum*".

Eikmanns et al.(1994) Microbiology 140:1817-1 828, "Nucleotide sequence, expression and transcriptional analysis. . . citrate synthase".

Bardford, Marion M. (1976) Anal. Biochem. 72:248-254, "A Rapid and Sensitive Method for the . . . Principle of Protein-Dye Binding".

Liebl et al. (1989) FEMS Microbiology Letters 53:299-303, "High efficiency electroporation of intact *Corynebacterium glutamicum*".

\* cited by examiner

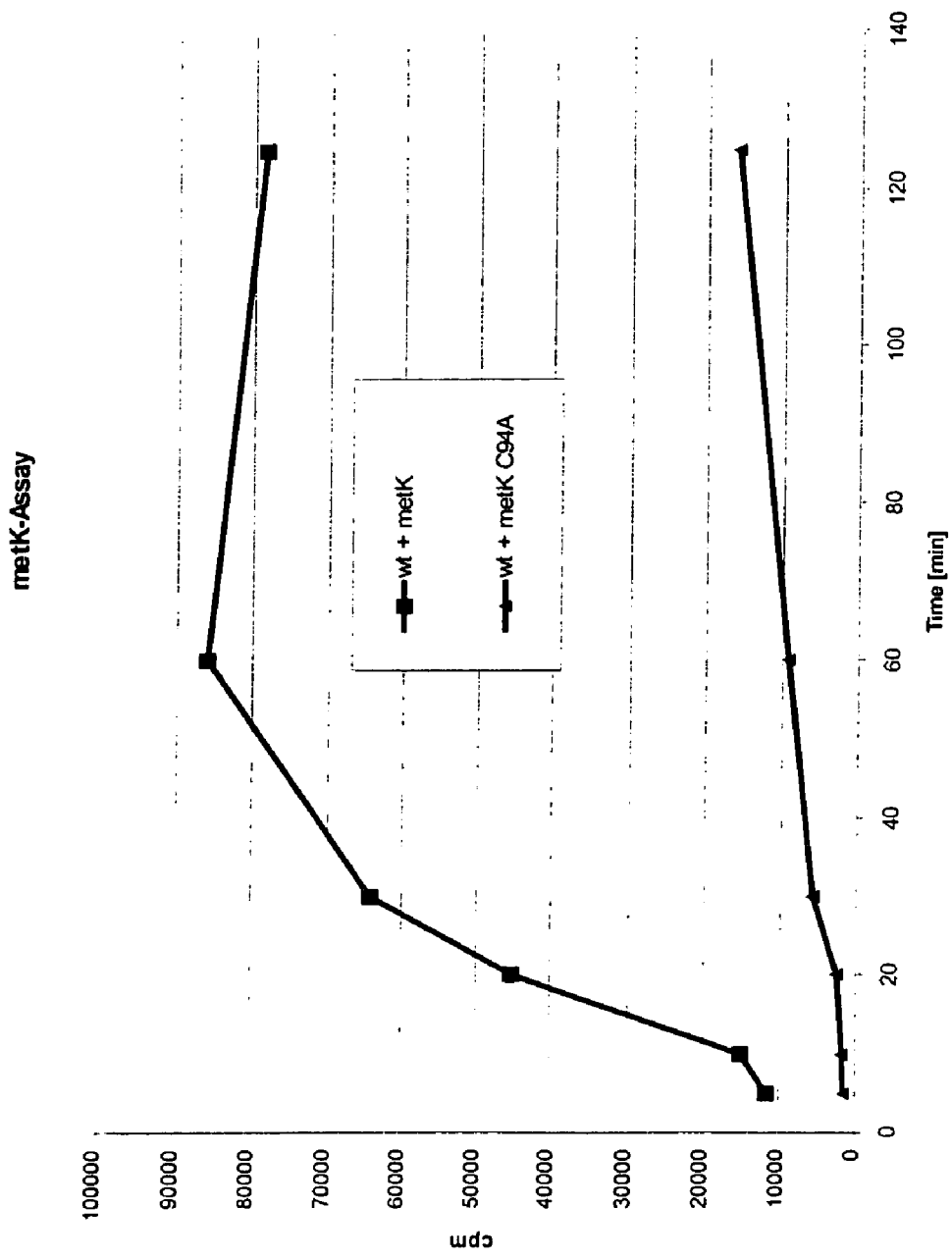

SEQUENCE LISTING

<160> NUMBER OF SEQ ID NOS: 23

<210> SEQ ID NO 1
<211> LENGTH: 52
<212> TYPE: DNA
<213> ORGANISM: Artificial Sequence
<220> FEATURE:
<223> OTHER INFORMATION: PCR primer

<400> SEQUENCE: 1
cccgggatcc gctagcggcg cgccggccgg cccggtgtga ataccgcac ag    52

<210> SEQ ID NO 2
<211> LENGTH: 53
<212> TYPE: DNA
<213> ORGANISM: Artificial Sequence
<220> FEATURE:
<223> OTHER INFORMATION: PCR primer

<400> SEQUENCE: 2
tctagactcg agcggccgcg gccggccttt aaattgaaga cgaaagggcc tcg    53

<210> SEQ ID NO 3
<211> LENGTH: 47
<212> TYPE: DNA
<213> ORGANISM: Artificial Sequence
<220> FEATURE:
<223> OTHER INFORMATION: PCR primer

<400> SEQUENCE: 3
gagatctaga cccggggatc cgctagcggg ctgctaaagg aagcgga    47

<210> SEQ ID NO 4
<211> LENGTH: 38
<212> TYPE: DNA
<213> ORGANISM: Artificial Sequence
<220> FEATURE:
<223> OTHER INFORMATION: PCR primer

<400> SEQUENCE: 4
gagaggcgcg ccgctagcgt gggcgaagaa ctccagca    38

<210> SEQ ID NO 5
<211> LENGTH: 34
<212> TYPE: DNA
<213> ORGANISM: Artificial Sequence
<220> FEATURE:
<223> OTHER INFORMATION: PCR primer

<400> SEQUENCE: 5
gagagggcgg ccgcgcaaag tcccgcttcg tgaa    34

<210> SEQ ID NO 6
<211> LENGTH: 34
<212> TYPE: DNA
<213> ORGANISM: Artificial Sequence
<220> FEATURE:
<223> OTHER INFORMATION: PCR primer

<400> SEQUENCE: 6
gagagggcgg ccgctcaagt cggtcaagcc acgc    34

<210> SEQ ID NO 7
<211> LENGTH: 140

```
<212> TYPE: DNA
<213> ORGANISM: Artificial Sequence
<220> FEATURE:
<223> OTHER INFORMATION: multiple cloning site

<400> SEQUENCE: 7
tcgaatttaa atctcgagag gcctgacgtc gggcccggta ccacgcgtca tatgactagt      60
tcggacctag ggatatcgtc gacatcgatg ctcttctgcg ttaattaaca attgggatcc     120
tctagacccg ggatttaaat                                                 140

<210> SEQ ID NO 8
<211> LENGTH: 140
<212> TYPE: DNA
<213> ORGANISM: Artificial Sequence
<220> FEATURE:
<223> OTHER INFORMATION: multiple cloning site

<400> SEQUENCE: 8
gatcatttaa atcccgggtc tagaggatcc caattgttaa ttaacgcaga agagcatcga      60
tgtcgacgat atccctaggt ccgaactagt catatgacgc gtggtaccgg gcccgacgtc     120
aggcctctcg agatttaaat                                                 140

<210> SEQ ID NO 9
<211> LENGTH: 5091
<212> TYPE: DNA
<213> ORGANISM: Artificial Sequence
<220> FEATURE:
<223> OTHER INFORMATION: Plasmid

<400> SEQUENCE: 9
tcgatttaaa tctcgagagg cctgacgtcg ggcccggtac cacgcgtcat atgactagtt      60
cggacctagg gatatcgtcg acatcgatgc tcttctgcgt taattaacaa ttgggatcct     120
ctagacccgg gatttaaatc gctagcgggc tgctaaagga agcggaacac gtagaaagcc    180
agtccgcaga aacggtgctg accccggatg aatgtcagct actgggctat ctggacaagg    240
gaaaacgcaa gcgcaaagag aaagcaggta gcttgcagtg gcttacatg gcgatagcta    300 gactgggcgg ttttatggac agcaagcgaa ccggaattgc cagctggggc gccctctggt    360
aaggttggga gcccgcaa agtaaactgg atggctttct tgccgccaag gatctgatgg    420
cgcaggggat caagatctga tcaagagaca ggatgaggat cgtttcgcat gattgaacaa    480
gatggattgc acgcaggttc tccggccgct gggtggaga ggctattcgg ctatgactgg    540
gcacaacaga caatcggctg ctctgatgcc gccgtgttcc ggctgtcagc gcaggggcgc    600
ccggttcttt ttgtcaagac cgacctgtcc ggtgccctga tgaactgca ggacgaggca    660 gcgcggctat cgtggctggc cacgacgggc gttccttgcg cagctgtgct cgacgttgtc    720
actgaagcgg gaagggactg gctgctattg ggcgaagtgc cggggcagga tctcctgtca    780
tctcaccttg ctcctgccga aaagtatcc atcatggctg atgcaatgcg gcggctgcat    840
acgcttgatc cggctacctg cccattcgac caccaagcga acatcgcat cgagcgagca    900 cgtactcgga tggaagccgg tcttgtcgat caggatgatc tggacgaaga gcatcagggg    960
ctcgcgccag ccgaactgtt cgccaggctc aaggcgcgca tgcccgacgg cgaggatctc   1020
gtcgtgaccc atggcgatgc ctgcttgccg aatatcatgg tggaaaatgg ccgcttttct   1080
ggattcatcg actgtggccg gctgggtgtg gcggaccgct atcaggacat agcgttggct   1140
acccgtgata ttgctgaaga gcttggcggc gaatgggctg accgcttcct cgtgctttac   1200
```

```
ggtatcgccg ctcccgattc gcagcgcatc gccttctatc gccttcttga cgagttcttc    1260
tgagcgggac tctggggttc gaaatgaccg accaagcgac gcccaacctg ccatcacgag    1320
atttcgattc caccgccgcc ttctatgaaa ggttgggctt cggaatcgtt ttccgggacg    1380
ccggctggat gatcctccag cgcggggatc tcatgctgga gttcttcgcc cacgctagcg    1440
gcgcgccggc cggcccggtg tgaaataccg cacagatgcg taaggagaaa ataccgcatc    1500
aggcgctctt ccgcttcctc gctcactgac tcgctgcgct cggtcgttcg gctgcggcga    1560
gcggtatcag ctcactcaaa ggcggtaata cggttatcca cagaatcagg gataacgca    1620 ggaaagaaca tgtgagcaaa aggccagcaa aaggccagga accgtaaaaa ggccgcgttg    1680
ctggcgtttt tccataggct ccgccccct gacgagcatc acaaaaatcg acgctcaagt    1740
cagaggtggc gaaacccgac aggactataa agataccagg cgtttccccc tggaagctcc    1800
ctcgtgcgct ctcctgttcc gaccctgccg cttaccggat acctgtccgc ctttctccct    1860
tcgggaagcg tggcgctttc tcatagctca cgctgtaggt atctcagttc ggtgtaggtc    1920
gttcgctcca agctgggctg tgtgcacgaa ccccccgttc agcccgaccg ctgcgcctta    1980
tccggtaact atcgtcttga gtccaacccg gtaagacacg acttatcgcc actggcagca    2040
gccactggta acaggattag cagagcgagg tatgtaggcg gtgctacaga gttcttgaag    2100
tggtggccta actacggcta cactagaagg acagtatttg gtatctgcgc tctgctgaag    2160
ccagttacct tcggaaaaag agttggtagc tcttgatccg gcaaacaaac caccgctggt    2220
agcggtggtt tttttgtttg caagcagcag attacgcgca gaaaaaaagg atctcaagaa    2280
gatcctttga tcttttctac ggggtctgac gctcagtgga acgaaaactc acgttaaggg    2340
attttggtca tgagattatc aaaaaggatc ttcacctaga tccttttaaa ggccggccgc    2400
ggccgcgcaa agtcccgctt cgtgaaaatt ttcgtgccgc gtgattttcc gccaaaaact    2460
ttaacgaacg ttcgttataa tggtgtcatg accttcacga cgaagtacta aaattggccc    2520
gaatcatcag ctatggatct ctctgatgtc gcgctggagt ccgacgcgct cgatgctgcc    2580
gtcgatttaa aaacggtgat cggattttc cgagctctcg atacgacgga cgcgccagca    2640
tcacgagact gggccagtgc cgcgagcgac ctagaaactc tcgtggcgga tcttgaggag    2700
ctggctgacg agctgcgtgc tcggccagcg ccaggaggac gcacagtagt ggaggatgca    2760
atcagttgcg cctactgcgg tggcctgatt cctccccggc ctgacccgcg aggacggcgc    2820
gcaaaatatt gctcagatgc gtgtcgtgcc gcagccagcc gcgagcgcgc aacaaacgc    2880 cacgccgagg agctggaggc ggctaggtcg caaatggcgc tggaagtgcg tcccccgagc    2940
gaaattttgg ccatggtcgt cacagagctg gaagcggcag cgagaattat cgcgatcgtg    3000
gcggtgcccg caggcatgac aaacatcgta aatgccgcgt ttcgtgtgcc gtggccgccc    3060
aggacgtgtc agcgccgcca ccacctgcac cgaatcggca gcagcgtcgc gcgtcgaaaa    3120
agcgcacagg cggcaagaag cgataagctg cacgaatacc tgaaaaatgt gaacgccc    3180 gtgagcggta actcacaggg cgtcggctaa ccccccagtcc aaacctggga gaaagcgctc    3240
aaaaatgact ctagcggatt cacgagacat tgacacaccg gctggaaat tttccgctga    3300 tctgttcgac acccatcccg agctcgcgct gcgatcacgt ggctggacga gcgaagaccg    3360
ccgcgaattc ctcgctcacc tgggcagaga aaatttccag ggcagcaaga cccgcgactt    3420
cgccagcgct tggatcaaag acccggacac ggagaaacac agccgaagtt ataccgagtt    3480
ggttcaaaat cgcttgcccg gtgccagtat gttgctctga cgcacgcgca gcacgcagcc    3540
gtgcttgtcc tggacattga tgtgccgagc caccaggccg gcgggaaaat cgagcacgta    3600
```

| | |
|---|---|
| aaccccgagg tctacgcgat tttggagcgc tgggcacgcc tggaaaaagc gccagcttgg | 3660 |
| atcggcgtga atccactgag cgggaaatgc cagctcatct ggctcattga tccggtgtat | 3720 |
| gccgcagcag gcatgagcag cccgaatatg cgcctgctgg ctgcaacgac cgaggaaatg | 3780 |
| acccgcgttt tcggcgctga ccaggctttt tcacataggc tgagccgtgg ccactgcact | 3840 |
| ctccgacgat cccagccgta ccgctggcat gcccagcaca atcgcgtgga tcgcctagct | 3900 |
| gatcttatgg aggttgctcg catgatctca ggcacagaaa aacctaaaaa acgctatgag | 3960 |
| caggagtttt ctagcggacg ggcacgtatc gaagcggcaa gaaaagccac tgcggaagca | 4020 |
| aaagcacttg ccacgcttga agcaagcctg ccgagcgccg ctgaagcgtc tggagagctg | 4080 |
| atcgacggcg tccgtgtcct ctggactgct ccagggcgtg ccgcccgtga tgagacggct | 4140 |
| tttcgccacg ctttgactgt gggataccag ttaaaagcgg ctggtgagcg cctaaaagac | 4200 |
| accaagggtc atcgagccta cgagcgtgcc tacaccgtcg ctcaggcggt cggaggaggc | 4260 |
| cgtgagcctg atctgccgcc ggactgtgac cgccagacgg attggccgcg acgtgtgcgc | 4320 |
| ggctacgtcg ctaaaggcca gccagtcgtc cctgctcgtc agacagagac gcagagccag | 4380 |
| ccgaggcgaa aagctctggc cactatggga agacgtggcg gtaaaaggc cgcagaacgc | 4440 |
| tggaaagacc caaacagtga gtacgcccga gcacagcgag aaaaactagc taagtccagt | 4500 |
| caacgacaag ctaggaaagc taaggaaat cgcttgacca ttgcaggttg gtttatgact | 4560 |
| gttgagggag agactggctc gtggccgaca atcaatgaag ctatgtctga atttagcgtg | 4620 |
| tcacgtcaga ccgtgaatag agcacttaag gtctgcgggc attgaacttc cacgaggacg | 4680 |
| ccgaaagctt cccagtaaat gtgccatctc gtaggcagaa aacggttccc ccgtagggtc | 4740 |
| tctctcttgg cctcctttct aggtcgggct gattgctctt gaagctctct aggggggctc | 4800 |
| acaccatagg cagataacgt tccccaccgg ctcgcctcgt aagcgcacaa ggactgctcc | 4860 |
| caaagatctt caaagccact gccgcgactg ccttcgcgaa gccttgcccc gcggaaattt | 4920 |
| cctccaccga gttcgtgcac accctatgc caagcttctt tcaccctaaa ttcgagagat | 4980 |
| tggattctta ccgtggaaat tcttcgcaaa atcgtcccc tgatcgccct tgcgacgttg | 5040 |
| gcgtcggtgc cgctggttgc gcttggcttg accgacttga tcagcggccg c | 5091 |

<210> SEQ ID NO 10
<211> LENGTH: 33
<212> TYPE: DNA
<213> ORGANISM: Artificial Sequence
<220> FEATURE:
<223> OTHER INFORMATION: PCR primer

<400> SEQUENCE: 10
gagagcggcc gccgatcctt tttaacccat cac    33

<210> SEQ ID NO 11
<211> LENGTH: 32
<212> TYPE: DNA
<213> ORGANISM: Artificial Sequence
<220> FEATURE:
<223> OTHER INFORMATION: PCR primer

<400> SEQUENCE: 11
aggagcggcc gccatcggca ttttcttttg cg    32

<210> SEQ ID NO 12
<211> LENGTH: 4323
<212> TYPE: DNA

<213> ORGANISM: Artificial Sequence
<220> FEATURE:
<223> OTHER INFORMATION: Plasmid

<400> SEQUENCE: 12

```
tcgagaggcc tgacgtcggg cccggtacca cgcgtcatat gactagttcg gacctaggga      60
tatcgtcgac atcgatgctc ttctgcgtta attaacaatt gggatcctct agacccggga     120
tttaaatcgc tagcgggctg ctaaaggaag cggaacacgt agaaagccag tccgcagaaa     180
cggtgctgac cccggatgaa tgtcagctac tgggctatct ggacaaggga aaacgcaagc     240
gcaaagagaa agcaggtagc ttgcagtggg cttacatggc gatagctaga ctgggcggtt     300
ttatggacag caagcgaacc ggaattgcca gctgggcgc  cctctggtaa ggttgggaag     360
ccctgcaaag taaactggat ggctttcttg ccgccaagga tctgatggcg caggggatca     420
agatctgatc aagagacagg atgaggatcg tttcgcatga ttgaacaaga tggattgcac     480
gcaggttctc cggccgcttg ggtggagagg ctattcggct atgactgggc acaacagaca     540
atcggctgct ctgatgccgc cgtgttccgg ctgtcagcgc aggggcgccc ggttcttttt     600
gtcaagaccg acctgtccgg tgccctgaat gaactgcagg acgaggcagc gcggctatcg     660
tggctggcca cgacgggcgt tccttgcgca gctgtgctcg acgttgtcac tgaagcggga     720
agggactggc tgctattggg cgaagtgccg gggcaggatc tcctgtcatc tcaccttgct     780
cctgccgaga agtatccat  catggctgat gcaatgcggc ggctgcatac gcttgatccg     840
gctacctgcc cattcgacca ccaagcgaaa catcgcatcg agcgagcacg tactcggatg     900
gaagccggtc ttgtcgatca ggatgatctg gacgaagagc atcagggct  cgcgccagcc     960
gaactgttcg ccaggctcaa ggcgcgcatg cccgacggcg aggatctcgt cgtgacccat    1020
ggcgatgcct gcttgccgaa tatcatggtg gaaaatggcc gcttttctgg attcatcgac    1080
tgtggccggc tgggtgtggc ggaccgctat caggacatag cgttggctac ccgtgatatt    1140
gctgaagagc ttggcggcga atgggctgac cgcttcctcg tgctttacgg tatcgccgct    1200
cccgattcgc agcgcatcgc cttctatcgc cttcttgacg agttcttctg agcgggactc    1260
tggggttcga aatgaccgac caagcgacgc ccaacctgcc atcacgagat ttcgattcca    1320
ccgccgcctt ctatgaaagg ttgggcttcg aatcgttttc cgggacgcc  ggctggatga    1380
tcctccagcg cggggatctc atgctggagt tcttcgccca cgctagcggc gcgccggccg    1440
gcccggtgtg aaataccgca cagatgcgta aggagaaaat accgcatcag gcgctcttcc    1500
gcttcctcgc tcactgactc gctgcgctcg gtcgttcggc tgcggcgagc ggtatcagct    1560
cactcaaagg cggtaatacg gttatccaca gaatcagggg ataacgcagg aaagaacatg    1620
tgagcaaaag gccagcaaaa ggccaggaac cgtaaaaagg ccgcgttgct ggcgtttttc    1680
cataggctcc gcccccctga cgagcatcac aaaaatcgac gctcaagtca gaggtggcga    1740
aacccgacag gactataaag ataccaggcg tttccccctg gaagctccct cgtgcgctct    1800
cctgttccga cctgccgct  taccggatac ctgtccgcct ttctcccttc gggaagcgtg    1860
gcgctttctc atagctcacg ctgtaggtat ctcagttcgg tgtaggtcgt tcgctccaag    1920
ctgggctgtg tgcacgaacc ccccgttcag cccgaccgct gcgccttatc cggtaactat    1980
cgtcttgagt ccaacccggt aagacacgac ttatcgccac tggcagcagc cactggtaac    2040
aggattagca gagcgaggta tgtaggcggt gctacagagt tcttgaagtg gtggcctaac    2100
tacggctaca ctagaaggac agtatttggt atctgcgctc tgctgaagcc agttaccttc    2160
ggaaaaagag ttggtagctc ttgatccggc aaacaaacca ccgctggtag cggtggtttt    2220
```

```
tttgtttgca agcagcagat tacgcgcaga aaaaaaggat ctcaagaaga tcctttgatc    2280
ttttctacgg ggtctgacgc tcagtggaac gaaaactcac gttaagggat tttggtcatg    2340
agattatcaa aaaggatctt cacctagatc cttttaaagg ccggccgcgg ccgccatcgg    2400
cattttcttt tgcgttttta tttgttaact gttaattgtc cttgttcaag gatgctgtct    2460
ttgacaacag atgttttctt gcctttgatg ttcagcagga agctcggcgc aaacgttgat    2520
tgtttgtctg cgtagaatcc tctgtttgtc atatagcttg taatcacgac attgtttcct    2580
ttcgcttgag gtacagcgaa gtgtgagtaa gtaaaggtta catcgttagg atcaagatcc    2640
atttttaaca aaggccagt tttgttcagc ggcttgtatg ggccagttaa agaattagaa     2700
acataaccaa gcatgtaaat atcgttagac gtaatgccgt caatcgtcat ttttgatccg    2760
cgggagtcag tgaacaggta ccatttgccg ttcattttaa agacgttcgc gcgttcaatt    2820
tcatctgtta ctgtgttaga tgcaatcagc ggtttcatca cttttttcag tgtgtaatca    2880
tcgtttagct caatcatacc gagagcgccg tttgctaact cagccgtgcg ttttttatcg    2940
ctttgcagaa gttttttgact tcttgacgg aagaatgatg tgcttttgcc atagtatgct     3000
ttgttaaata aagattcttc gccttggtag ccatcttcag ttccagtgtt tgcttcaaat    3060
actaagtatt tgtggccttt atcttctacg tagtgaggat ctctcagcgt atggttgtcg    3120
cctgagctgt agttgccttc atcgatgaac tgctgtacat tttgatacgt ttttccgtca    3180
ccgtcaaaga ttgatttata atcctctaca ccgttgatgt tcaaagagct gtctgatgct    3240
gatacgttaa cttgtgcagt tgtcagtgtt tgtttgccgt aatgtttacc ggagaaatca    3300
gtgtagaata aacggatttt tccgtcagat gtaaatgtgg ctgaacctga ccattcttgt    3360
gtttggtctt ttaggataga atcatttgca tcgaatttgt cgctgtcttt aaagacgcgg    3420
ccagcgtttt tccagctgtc aatagaagtt tcgccgactt tttgatagaa catgtaaatc    3480
gatgtgtcat ccgcattttt aggatctccg gctaatgcaa agacgatgtg gtagccgtga    3540
tagtttgcga cagtgccgtc agcgttttgt aatggccagc tgtcccaaac gtccaggcct    3600
tttgcagaag agatattttt aattgtggac gaatcaaatt cagaaacttg atattttca     3660 ttttttttgct gttcagggat ttgcagcata tcatggcgtg taatatggga aatgccgtat    3720
gttttcctta tatggctttg gttcgttct ttcgcaaacg cttgagttgc gcctcctgcc     3780
agcagtgcgg tagtaaaggt taatactgtt gcttgtttg caaactttt gatgttcatc      3840 gttcatgtct cctttttat gtactgtgtt agcggtctgc ttcttccagc cctcctgttt     3900
gaagatggca agttagttac gcacaataaa aaaagaccta aaatatgtaa ggggtgacgc    3960
caaagtatac actttgccct ttacacattt taggtcttgc ctgctttatc agtaacaaac    4020
ccgcgcgatt tacttttcga cctcattcta ttagactctc gtttggattg caactggtct    4080
attttcctct tttgtttgat agaaaatcat aaaaggattt gcagactacg ggcctaaaga    4140
actaaaaaat ctatctgttt cttttcattc tctgtatttt ttatagtttc tgttgcatgg    4200
gcataaagtt gccttttta tcacaattca gaaaatatca taatatctca tttcactaaa    4260
taatagtgaa cggcaggtat atgtgatggg ttaaaaagga tcggcggccg ctcgatttaa    4320
atc                                                                  4323
```

<210> SEQ ID NO 13
<211> LENGTH: 34
<212> TYPE: DNA
<213> ORGANISM: Artificial Sequence
<220> FEATURE:

-continued

<223> OTHER INFORMATION: PCR primer

<400> SEQUENCE: 13
gagagcccgg gaagaagggc tgcgacctcc tcat                                34

<210> SEQ ID NO 14
<211> LENGTH: 34
<212> TYPE: DNA
<213> ORGANISM: Artificial Sequence
<220> FEATURE:
<223> OTHER INFORMATION: PCR primer

<400> SEQUENCE: 14
ctctcacgcg tcatatgcag gtgaggtaac ccca                                34

<210> SEQ ID NO 15
<211> LENGTH: 6631
<212> TYPE: DNA
<213> ORGANISM: Artificial Sequence
<220> FEATURE:
<223> OTHER INFORMATION: Plasmid

<400> SEQUENCE: 15

| | |
|---|---|
| cgcgtcatat gcaggtgagg taaccccaaa agaggtaaaa cccgcgccac cgacttttca | 60 |
| ggagcgggga cgcgggtttt tgccatgaat ccgaagatac tacatcagat ttttaggcca | 120 |
| acttgagggc tgcgcgaagt tcatcaacgc ggtcgatagc ctcccaagga aggtccaaat | 180 |
| cagtgcgacc aaagtggccg taggcagcag tgtcagcgta gatcggacga agcagatcaa | 240 |
| gctcacggat aattgctgct ggacgcaggt caaagacctc caacacggca gcctgaatct | 300 |
| gctcgtcgct caggccttcc ttgttggtgt caaaggtttc aacgtaaagt ccgactggct | 360 |
| tgcgcgtcc aatggcgtat gcaacctgaa cttcagcgcg atcagcaagg cctgctgcca | 420 |
| cgatgttctt tgctacccaa cgcatggcgt atgcagcaga gcgtccacc ttgcttggat | 480 |
| ccttaccgga gaatgctcca ccaccatggc gagccatgcc accgtaggta tccacgatga | 540 |
| tcttgcggcc ggtcagaccc gcatcaccca tggggccacc cagaatgaag gaacctgaag | 600 |
| ggttgatcaa cacggtgatc tcaccggttg ccagatcctc aatgcctgcg tctttgatta | 660 |
| cccaatcaat gacgtgttcg cgcagttggg tttccaacca tgcacggtca acttctgggt | 720 |
| cgtgctgggt ggagatgaca acggtatcca ggtggctagg gcggtcttgc gcatcgtatg | 780 |
| cgaaggtgac ctgggttttt ccgtctggac gcaggtgagg aacgatgccc tctttacgaa | 840 |
| cctgggtcag acgacgtgac agtcggtgcg ccaacgcgat aggaagaggc atgtactctt | 900 |
| cggtttcgtt ggtggcgtag ccgaacatca ggccctggtc gccagcacct gcgcggtcgt | 960 |
| cttcttcaac gtcgccgttg gtgcgggctt cgtcggagtt atccacgccg tcagcgattt | 1020 |
| cctgggactg ctcaccgatg gatactgaga cgccacaggt gcgtccgtcg aatccaacct | 1080 |
| cagaggagtt gaatccgatt tcgatgagct tgttgcggac taattgaggg atctctacgt | 1140 |
| aagcgctggt acggacctcg ccaacaacat ggacgattcc ggtggtgacc acagtttcca | 1200 |
| ctgcgacgcg cgactgcgga tctttttcga gcagcgcgtc caaatggta tcggaaatag | 1260 |
| catcacatat tttgtctgga tgtccctcag ttacagattc actggtgaac aaacggacgg | 1320 |
| cggttggctg agccacaaat accctttcctt cgaagaagtt gagaataaat agtcttaaat | 1380 |
| acaaaaaacc aatatagacc aagctgtcta aaactgcaat gtcagtggtc tagctggatt | 1440 |
| tttctagact tcgcgatacg ccagtgccgc gtcccaaatt tgcgcagcaa cctcgatttt | 1500 |
| gctgccgtgc tccacatcga ctaccccacc gtgagcatcc aaaatccagc cctcattgtg | 1560 |

-continued

```
cttttgccca aacactttgc ccatgcccac ctcattacac atgaggaggt cgcagccctt    1620
cttcccggga tttaaatcgc tagcgggctg ctaaaggaag cggaacacgt agaaagccag    1680
tccgcagaaa cggtgctgac cccggatgaa tgtcagctac tgggctatct ggacaaggga    1740
aaacgcaagc gcaaagagaa agcaggtagc ttgcagtggg cttacatggc gatagctaga    1800
ctgggcggtt ttatggacag caagcgaacc ggaattgcca gctggggcgc cctctggtaa    1860
ggttgggaag ccctgcaaag taaactggat ggctttcttg ccgccaagga tctgatggcg    1920
caggggatca agatctgatc aagagacagg atgaggatcg tttcgcatga ttgaacaaga    1980
tggattgcac gcaggttctc cggccgcttg ggtggagagg ctattcggct atgactgggc    2040
acaacagaca atcggctgct ctgatgccgc cgtgttccgg ctgtcagcgc aggggcgccc    2100
ggttcttttt gtcaagaccg acctgtccgg tgccctgaat gaactgcagg acgaggcagc    2160
gcggctatcg tggctggcca cgacgggcgt tccttgcgca gctgtgctcg acgttgtcac    2220
tgaagcggga agggactggc tgctattggg cgaagtgccg gggcaggatc tcctgtcatc    2280
tcaccttgct cctgccgaga agtatccat catggctgat gcaatgcggc ggctgcatac    2340
gcttgatccg gctacctgcc cattcgacca ccaagcgaaa catcgcatcg agcgagcacg    2400
tactcggatg aagccggtc ttgtcgatca ggatgatctg gacgaagagc atcaggggct    2460
cgcgccagcc gaactgttcg ccaggctcaa ggcgcgcatg cccgacggcg aggatctcgt    2520
cgtgacccat ggcgatgcct gcttgccgaa tatcatggtg aaaatggcc gcttttctgg    2580
attcatcgac tgtggccggc tgggtgtggc ggaccgctat caggacatag cgttggctac    2640
ccgtgatatt gctgaagagc ttggcggcga atgggctgac cgcttcctcg tgctttacgg    2700
tatcgccgct cccgattcgc agcgcatcgc cttctatcgc cttcttgacg agttcttctg    2760
agcgggactc tggggttcga atgaccgac caagcgacgc ccaacctgcc atcacgagat    2820
ttcgattcca ccgccgcctt ctatgaaagg ttgggcttcg gaatcgtttt ccggacgcc    2880
ggctggatga tcctccagcg cggggatctc atgctggagt tcttcgccca cgctagcggc    2940
gcgccggccg gccggtgtg aaataccgca cagatgcgta aggagaaaat accgcatcag    3000
gcgctcttcc gcttcctcgc tcactgactc gctgcgctcg gtcgttcggc tgcggcgagc    3060
ggtatcagct cactcaaagg cggtaatacg gttatccaca gaatcagggg ataacgcagg    3120
aaagaacatg tgagcaaaag gccagcaaaa ggccaggaac cgtaaaaagg ccgcgttgct    3180
ggcgtttttc cataggctcc gcccccctga cgagcatcac aaaaatcgac gctcaagtca    3240
gaggtggcga aacccgacag gactataaag ataccaggcg tttccccctg gaagctccct    3300
cgtgcgctct cctgttccga ccctgccgct taccggatac ctgtccgcct ttctcccttc    3360
gggaagcgtg gcgctttctc atagctcacg ctgtaggtat ctcagttcgg tgtaggtcgt    3420
tcgctccaag ctgggctgtg tgcacgaacc ccccgttcag cccgaccgct gcgccttatc    3480
cggtaactat cgtcttgagt ccaacccggt aagacacgac ttatcgccac tggcagcagc    3540
cactggtaac aggattagca gagcgaggta tgtaggcggt gctacagagt tcttgaagtg    3600
gtggcctaac tacggctaca ctagaaggac agtatttggt atctgcgctc tgctgaagcc    3660
agttaccttc ggaaaaagag ttggtagctc ttgatccggc aaacaaacca ccgctggtag    3720
cggtggtttt tttgtttgca agcagcagat tacgcgcaga aaaaaaggat ctcaagaaga    3780
tcctttgatc ttttctacgg ggtctgacgc tcagtggaac gaaaactcac gttaagggat    3840
tttggtcatg agattatcaa aaaggatctt cacctagatc cttttaaagg ccggccgcgg    3900
```

```
ccgcgcaaag tcccgcttcg tgaaaatttt cgtgccgcgt gattttccgc caaaaacttt   3960
aacgaacgtt cgttataatg gtgtcatgac cttcacgacg aagtactaaa attggcccga   4020
atcatcagct atggatctct ctgatgtcgc gctggagtcc gacgcgctcg atgctgccgt   4080
cgatttaaaa acggtgatcg gattttccg agctctcgat acgacggacg cgccagcatc    4140
acgagactgg gccagtgccg cgagcgacct agaaactctc gtggcggatc ttgaggagct   4200
ggctgacgag ctgcgtgctc ggccagcgcc aggaggacgc acagtagtgg aggatgcaat   4260
cagttgcgcc tactgcggtg gcctgattcc tccccggcct gacccgcgag gacggcgcgc   4320
aaaatattgc tcagatgcgt gtcgtgccgc agccagccgc gagcgcgcca acaaacgcca   4380
cgccgaggag ctggaggcgg ctaggtcgca aatggcgctg gaagtgcgtc ccccgagcga   4440
aattttggcc atggtcgtca cagagctgga agcggcagcg agaattatcg cgatcgtggc   4500
ggtgcccgca ggcatgacaa acatcgtaaa tgccgcgttt cgtgtgccgt ggccgcccag   4560
gacgtgtcag cgccgccacc acctgcaccg aatcggcagc agcgtcgcgc gtcgaaaaag   4620
cgcacaggcg gcaagaagcg ataagctgca cgaatacctg aaaaatgttg aacgccccgt   4680
gagcggtaac tcacagggcg tcggctaacc cccagtccaa acctgggaga aagcgctcaa   4740
aaatgactct agcggattca cgagacattg acacaccggc ctggaaattt tccgctgatc   4800
tgttcgacac ccatcccgag ctcgcgctgc gatcacgtgg ctggacgagc gaagaccgcc   4860
gcgaattcct cgctcacctg ggcagagaaa atttccaggg cagcaagacc cgcgacttcg   4920
ccagcgcttg gatcaaagac ccggacacgg agaaacacag ccgaagttat accgagttgg   4980
ttcaaaatcg cttgcccggt gccagtatgt tgctctgacg cacgcgcagc acgcagccgt   5040
gcttgtcctg gacattgatg tgccgagcca ccaggccggc gggaaaatcg agcacgtaaa   5100
ccccgaggtc tacgcgattt tggagcgctg ggcacgcctg gaaaaagcgc cagcttggat   5160
cggcgtgaat ccactgagcg ggaaatgcca gctcatctgg ctcattgatc cggtgtatgc   5220
cgcagcaggc atgagcagcc cgaatatgcg cctgctggct gcaacgaccg aggaaatgac   5280
ccgcgttttc ggcgctgacc aggctttttc acataggctg agccgtgcc actgcactct     5340 ccgacgatcc cagccgtacc gctggcatgc ccagcacaat cgcgtggatc gcctagctga   5400
tcttatggag gttgctcgca tgatctcagg cacagaaaaa cctaaaaaac gctatgagca   5460
ggagttttct agcggacggg cacgtatcga agcggcaaga aaagccactg cggaagcaaa   5520
agcacttgcc acgcttgaag caagcctgcc gagcgccgct gaagcgtctg gagagctgat   5580
cgacggcgtc cgtgtcctct ggactgctcc agggcgtgcc gcccgtgatg agacggcttt   5640
tcgccacgct ttgactgtgg gataccagtt aaaagcggct ggtgagcgcc taaaagacac   5700
caagggtcat cgagcctacg agcgtgccta caccgtcgct caggcggtcg gaggaggccg   5760
tgagcctgat ctgccgccgg actgtgaccg ccagacggat tggccgcgac gtgtgcgcgg   5820
ctacgtcgct aaaggccagc cagtcgtccc tgctcgtcag acagagacgc agagccagcc   5880
gaggcgaaaa gctctggcca ctatgggaag acgtggcggt aaaaaggccg cagaacgctg   5940
gaaagaccca acagtgagt acgcccgagc acagcgagaa aaactagcta agtccagtca    6000
acgacaagct aggaaagcta aggaaatcg cttgaccatt gcaggttggt ttatgactgt    6060
tgagggagag actggctcgt ggccgacaat caatgaagct atgtctgaat ttagcgtgtc   6120
acgtcagacc gtgaatagag cacttaaggt ctgcgggcat tgaacttcca cgaggacgcc   6180
gaaagcttcc cagtaaatgt gccatctcgt aggcagaaaa cggttccccc gtagggtctc   6240
tctcttggcc tcctttctag gtcgggctga ttgctcttga agctctctag gggggctcac   6300
```

```
accataggca gataacgttc cccaccggct cgcctcgtaa gcgcacaagg actgctccca    6360
aagatcttca aagccactgc cgcgactgcc ttcgcgaagc cttgccccgc ggaaatttcc    6420
tccaccgagt tcgtgcacac ccctatgcca agcttctttc accctaaatt cgagagattg    6480
gattcttacc gtggaaattc ttcgcaaaaa tcgtcccctg atcgcccttg cgacgttggc    6540
gtcggtgccg ctggttgcgc ttggcttgac cgacttgatc agcggccgct cgatttaaat    6600
ctcgagaggc ctgacgtcgg gcccggtacc a                                   6631
```

<210> SEQ ID NO 16
<211> LENGTH: 407
<212> TYPE: PRT
<213> ORGANISM: Corynebacterium glutamicum

<400> SEQUENCE: 16

```
Val Ala Gln Pro Thr Ala Val Arg Leu Phe Thr Ser Glu Ser Val Thr
1               5                   10                  15

Glu Gly His Pro Asp Lys Ile Cys Asp Ala Ile Ser Asp Thr Ile Leu
            20                  25                  30

Asp Ala Leu Leu Glu Lys Asp Pro Gln Ser Arg Val Ala Val Glu Thr
        35                  40                  45

Val Val Thr Thr Gly Ile Val His Val Val Gly Glu Val Arg Thr Ser
    50                  55                  60

Ala Tyr Val Glu Ile Pro Gln Leu Val Arg Asn Lys Leu Ile Glu Ile
65                  70                  75                  80

Gly Phe Asn Ser Ser Glu Val Gly Phe Asp Gly Arg Thr Cys Gly Val
                85                  90                  95

Ser Val Ser Ile Gly Glu Gln Ser Gln Glu Ile Ala Asp Gly Val Asp
            100                 105                 110

Asn Ser Asp Glu Ala Arg Thr Asn Gly Asp Val Glu Glu Asp Asp Arg
        115                 120                 125

Ala Gly Ala Gly Asp Gln Gly Leu Met Phe Gly Tyr Ala Thr Asn Glu
    130                 135                 140

Thr Glu Glu Tyr Met Pro Leu Pro Ile Ala Leu Ala His Arg Leu Ser
145                 150                 155                 160

Arg Arg Leu Thr Gln Val Arg Lys Glu Gly Ile Val Pro His Leu Arg
                165                 170                 175

Pro Asp Gly Lys Thr Gln Val Thr Phe Ala Tyr Asp Ala Gln Asp Arg
            180                 185                 190

Pro Ser His Leu Asp Thr Val Val Ile Ser Thr Gln His Asp Pro Glu
        195                 200                 205

Val Asp Arg Ala Trp Leu Glu Thr Gln Leu Arg Glu His Val Ile Asp
    210                 215                 220

Trp Val Ile Lys Asp Ala Gly Ile Glu Asp Leu Ala Thr Gly Glu Ile
225                 230                 235                 240

Thr Val Leu Ile Asn Pro Ser Gly Ser Phe Ile Leu Gly Gly Pro Met
                245                 250                 255

Gly Asp Ala Gly Leu Thr Gly Arg Lys Ile Ile Val Asp Thr Tyr Gly
            260                 265                 270

Gly Met Ala Arg His Gly Gly Gly Ala Phe Ser Gly Lys Asp Pro Ser
        275                 280                 285

Lys Val Asp Arg Ser Ala Ala Tyr Ala Met Arg Trp Val Ala Lys Asn
    290                 295                 300

Ile Val Ala Ala Gly Leu Ala Asp Arg Ala Glu Val Gln Val Ala Tyr
```

```
            305                 310                 315                 320
Ala Ile Gly Arg Ala Lys Pro Val Gly Leu Tyr Val Glu Thr Phe Asp
325                 330                 335

Thr Asn Lys Glu Gly Leu Ser Asp Glu Gln Ile Gln Ala Ala Val Leu
340                 345                 350

Glu Val Phe Asp Leu Arg Pro Ala Ala Ile Ile Arg Glu Leu Asp Leu
355                 360                 365

Leu Arg Pro Ile Tyr Ala Asp Thr Ala Ala Tyr Gly His Phe Gly Arg
370                 375                 380

Thr Asp Leu Asp Leu Pro Trp Glu Ala Ile Asp Arg Val Asp Glu Leu
385                 390                 395                 400

Arg Ala Ala Leu Lys Leu Ala
405

<210> SEQ ID NO 17
<211> LENGTH: 38
<212> TYPE: DNA
<213> ORGANISM: Artificial Sequence
<220> FEATURE:
<223> OTHER INFORMATION: PCR primer

<400> SEQUENCE: 17
gattcgacgg acgcaccgct ggcgtctcag tatccatc                              38

<210> SEQ ID NO 18
<211> LENGTH: 38
<212> TYPE: DNA
<213> ORGANISM: Artificial Sequence
<220> FEATURE:
<223> OTHER INFORMATION: PCR primer

<400> SEQUENCE: 18
gatggatact gagacgccag cggtgcgtcc gtcgaatc                              38

<210> SEQ ID NO 19
<211> LENGTH: 6631
<212> TYPE: DNA
<213> ORGANISM: Artificial Sequence
<220> FEATURE:
<223> OTHER INFORMATION: Plasmid

<400> SEQUENCE: 19
cgcgtcatat gcaggtgagg taaccccaaa agaggtaaaa cccgcgccac cgacttttca     60
ggagcgggga cgcgggtttt tgccatgaat ccgaagatac tacatcagat ttttaggcca    120
acttgagggc tgcgcgaagt tcatcaacgc ggtcgatagc ctcccaagga aggtccaaat    180
cagtgcgacc aaagtggccg taggcagcag tgtcagcgta gatcggacga agcagatcaa    240
gctcacggat aattgctgct ggacgcaggt caaagacctc caacacggca gcctgaatct    300
gctcgtcgct caggccttcc ttgttggtgt caaaggtttc aacgtaaagt ccgactggct    360
ttgcgcgtcc aatggcgtat gcaacctgaa cttcagcgcg atcagcaagg cctgctgcca    420
cgatgttctt tgctacccaa cgcatggcgt atgcagcaga gcgtccacc ttgcttggat    480 ccttaccgga gaatgctcca ccaccatggc gagccatgcc accgtaggta tccacgatga    540
tcttgcggcc ggtcagaccc gcatcaccca tgggccacc cagaatgaag gaacctgaag    600
ggttgatcaa cacggtgatc tcaccggttg ccagatcctc aatgcctgcg tctttgatta    660
cccaatcaat gacgtgttcg cgcagttggg tttccaacca tgcacggtca acttctgggt    720
cgtgctgggt ggagatgaca acggtatcca ggtggctagg gcggtcttgc gcatcgtatg    780
```

-continued

```
cgaaggtgac ctgggttttt ccgtctggac gcaggtgagg aacgatgccc tctttacgaa    840
cctgggtcag acgacgtgac agtcggtgcg ccaacgcgat aggaagaggc atgtactctt    900
cggtttcgtt ggtggcgtag ccgaacatca ggccctggtc gccagcacct gcgcggtcgt    960
cttcttcaac gtcgccgttg gtgcgggctt cgtcggagtt atccacgccg tcagcgattt   1020
cctgggactg ctcaccgatg gatactgaga cgccagcggt gcgtccgtcg aatccaacct   1080
cagaggagtt gaatccgatt tcgatgagct tgttgcggac taattgaggg atctctacgt   1140
aagcgctggt acggacctcg ccaacaacat ggacgattcc ggtggtgacc acagtttcca   1200
ctgcgacgcg cgactgcgga tcttttcga gcagcgcgtc caaaatggta tcggaaatag   1260
catcacatat tttgtctgga tgtccctcag ttacagattc actggtgaac aaacggacgg   1320
cggttggctg agccacaaat accttctt cgaagaagtt gagaataaat agtcttaaat   1380
acaaaaaacc aatatagacc aagctgtcta aaactgcaat gtcagtggtc tagctggatt   1440
tttctagact tcgcgatacg ccagtgccgc gtcccaaatt tgcgcagcaa cctcgatttt   1500
gctgccgtgc tccacatcga ctaccccacc gtgagcatcc aaaatccagc cctcattgtg   1560
cttttgccca aacactttgc ccatgcccac ctcattacac atgaggaggt cgcagccctt   1620
cttcccggga tttaaatcgc tagcgggctg ctaaaggaag cggaacacgt agaaagccag   1680
tccgcagaaa cggtgctgac cccggatgaa tgtcagctac tgggctatct ggacaaggga   1740
aaacgcaagc gcaaagagaa agcaggtagc ttgcagtggg cttacatggc gatagctaga   1800
ctgggcggtt ttatgacag caagcgaacc ggaattgcca gctggggcgc cctctggtaa   1860
ggttgggaag ccctgcaaag taaactggat ggctttcttg ccgccaagga tctgatggcg   1920
caggggatca agatctgatc aagagacagg atgaggatcg tttcgcatga ttgaacaaga   1980
tggattgcac gcaggttctc cggccgcttg ggtggagagg ctattcggct atgactgggc   2040
acaacagaca atcggctgct ctgatgccgc cgtgttccgg ctgtcagcgc aggggcgccc   2100
ggttcttttt gtcaagaccg acctgtccgg tgccctgaat gaactgcagg acgaggcagc   2160
gcggctatcg tggctggcca cgacgggcgt tccttgcgca gctgtgctcg acgttgtcac   2220
tgaagcggga agggactggc tgctattggg cgaagtgccg gggcaggatc tcctgtcatc   2280
tcaccttgct cctgccgaga aagtatccat catggctgat gcaatgcggc ggctgcatac   2340
gcttgatccg gctacctgcc cattcgacca ccaagcgaaa catcgcatcg agcgagcacg   2400
tactcggatg gaagccggtc ttgtcgatca ggatgatctg gacgaagagc atcaggggct   2460
cgcgccagcc gaactgttcg ccaggctcaa ggcgcgcatg cccgacggcg aggatctcgt   2520
cgtgacccat ggcgatgcct gcttgccgaa tatcatggtg aaaatggcc gcttttctgg   2580
attcatcgac tgtggccggc tgggtgtggc ggaccgctat caggacatag cgttggctac   2640
ccgtgatatt gctgaagagc ttggcggcga atgggctgac cgcttcctcg tgctttacgg   2700
tatcgccgct cccgattcgc agcgcatcgc cttctatcgc cttcttgacg agttcttctg   2760
agcgggactc tggggttcga atgaccgac caagcgacgc ccaacctgcc atcacgagat   2820
ttcgattcca ccgccgcctt ctatgaaagg ttgggcttcg aatcgttttt ccgggacgcc   2880
ggctggatga tcctccagcg cggggatctc atgctggagt tcttcgccca cgctagcggc   2940
gcgccggccg gcccggtgtg aaataccgca cagatgcgta aggagaaaat accgcatcag   3000
gcgctcttcc gcttcctcgc tcactgactc gctgcgctcg gtcgttcggc tgcggcgagc   3060
ggtatcagct cactcaaagg cggtaatacg gttatccaca gaatcagggg ataacgcagg   3120
```

```
aaagaacatg tgagcaaaag gccagcaaaa ggccaggaac cgtaaaaagg ccgcgttgct   3180
ggcgttttc  cataggctcc gcccccctga cgagcatcac aaaaatcgac gctcaagtca   3240
gaggtggcga acccgacag  gactataaag ataccaggcg tttccccctg gaagctccct   3300
cgtgcgctct cctgttccga ccctgccgct taccggatac ctgtccgcct ttctcccttc   3360
gggaagcgtg gcgctttctc atagctcacg ctgtaggtat ctcagttcgg tgtaggtcgt   3420
tcgctccaag ctgggctgtg tgcacgaacc ccccgttcag cccgaccgct gcgccttatc   3480
cggtaactat cgtcttgagt ccaacccggt aagacacgac ttatcgccac tggcagcagc   3540
cactggtaac aggattagca gagcgaggta tgtaggcggt gctacagagt tcttgaagtg   3600
gtggcctaac tacggctaca ctagaaggac agtatttggt atctgcgctc tgctgaagcc   3660
agttaccttc ggaaaaagag ttggtagctc ttgatccggc aaacaaacca ccgctggtag   3720
cggtggtttt tttgtttgca agcagcagat tacgcgcaga aaaaaggat  ctcaagaaga   3780
tcctttgatc ttttctacgg ggtctgacgc tcagtggaac gaaaactcac gttaagggat   3840
tttggtcatg agattatcaa aaaggatctt cacctagatc cttttaaagg ccggccgcgg   3900
ccgcgcaaag tcccgcttcg tgaaaatttt cgtgccgcgt gattttccgc caaaaacttt   3960
aacgaacgtt cgttataatg gtgtcatgac cttcacgacg aagtactaaa attggcccga   4020
atcatcagct atggatctct ctgatgtcgc gctggagtcc gacgcgctcg atgctgccgt   4080
cgatttaaaa acgtgatcg  gattttccg  agctctcgat acgacggacg cgccagcatc   4140
acgagactgg gccagtgccg cgagcgacct agaaactctc gtggcggatc ttgaggagct   4200
ggctgacgag ctgcgtgctc ggccagcgcc aggaggacgc acagtagtgg aggatgcaat   4260
cagttgcgcc tactgcggtg gcctgattcc tccccggcct gacccgcgag acggcgcgc   4320
aaaatattgc tcagatgcgt gtcgtgccgc agccagccgc gagcgcgcca acaaacgcca   4380
cgccgaggag ctgaggcgg  ctaggtcgca aatggcgctg gaagtgcgtc ccccgagcga   4440
aattttggcc atggtcgtca cagagctgga agcggcagcg agaattatcg cgatcgtggc   4500
ggtgcccgca ggcatgacaa acatcgtaaa tgccgcgttt cgtgtgccgt ggccgcccag   4560
gacgtgtcag cgccgccacc acctgcaccg aatcggcagc agcgtcgcgc gtcgaaaaag   4620
cgcacaggcg gcaagaagcg ataagctgca cgaatacctg aaaaatgttg aacgccccgt   4680
gagcggtaac tcacagggcg tcggctaacc cccagtccaa acctgggaga aagcgctcaa   4740
aaatgactct agcggattca cgagacattg acacaccggc ctggaaattt tccgctgatc   4800
tgttcgacac ccatcccgag ctcgcgctgc gatcacgtgg ctggacgagc gaagaccgcc   4860
gcgaattcct cgctcacctg ggcagagaaa atttccaggg cagcaagacc gcgacttcg   4920
ccagcgcttg gatcaaagac ccggacacgg agaaacacag ccgaagttat accgagttgg   4980
ttcaaaatcg cttgcccggt gccagtatgt tgctctgacg cacgcgcagc acgcagccgt   5040
gcttgtcctg gacattgatg tgccgagcca ccaggccggc gggaaaatcg agcacgtaaa   5100
ccccgaggtc tacgcgattt tggagcgctg ggcacgcctg gaaaaagcgc gagcttggat   5160
cggcgtgaat ccactgagcg ggaaatgcca gctcatctgg ctcattgatc cggtgtatgc   5220
cgcagcaggc atgagcagcc gaatatgcg  cctgctggct gcaacgaccg aggaaatgac   5280
ccgcgttttc ggcgctgacc aggcttttc  acataggctg agccgtggcc actgcactct   5340
ccgacgatcc cagccgtacc gctggcatgc ccagcacaat cgcgtggatc gcctagctga   5400
tcttatggag gttgctcgca tgatctcagg cacagaaaaa cctaaaaaac gctatgagca   5460
ggagttttct agcggacggg cacgtatcga agcggcaaga aaagccactg cggaagcaaa   5520
```

```
agcacttgcc acgcttgaag caagcctgcc gagcgccgct gaagcgtctg gagagctgat    5580
cgacggcgtc cgtgtcctct ggactgctcc agggcgtgcc gcccgtgatg agacggcttt    5640
tcgccacgct ttgactgtgg gataccagtt aaaagcggcg ggtgagcgcc taaaagacac    5700
caagggtcat cgagcctacg agcgtgccta caccgtcgct caggcggtcg gaggaggccg    5760
tgagcctgat ctgccgccgg actgtgaccg ccagacggat tggccgcgac gtgtgcgcgg    5820
ctacgtcgct aaaggccagc cagtcgtccc tgctcgtcag acagagacgc agagccagcc    5880
gaggcgaaaa gctctggcca ctatgggaag acgtggcggt aaaaaggccg cagaacgctg    5940
gaaagaccca acagtgagt acgcccgagc acagcgagaa aaactagcta agtccagtca    6000
acgacaagct aggaaagcta aggaaatcg cttgaccatt gcaggttggt ttatgactgt    6060
tgagggagag actggctcgt ggccgacaat caatgaagct atgtctgaat ttagcgtgtc    6120
acgtcagacc gtgaatagag cacttaaggt ctgcgggcat tgaacttcca cgaggacgcc    6180
gaaagcttcc cagtaaatgt gccatctcgt aggcagaaaa cggttccccc gtagggtctc    6240
tctcttggcc tcctttctag gtcgggctga ttgctcttga agctctctag ggggctcac    6300
accataggca gataacgttc cccaccggct cgcctcgtaa gcgcacaagg actgctccca    6360
aagatcttca aagccactgc cgcgactgcc ttcgcgaagc cttgcccgc ggaaatttcc    6420
tccaccgagt tcgtgcacac ccctatgcca agcttctttc accctaaatt cgagagattg    6480
gattcttacc gtggaaattc ttcgcaaaaa tcgtcccctg atcgcccttg cgacgttggc    6540
gtcggtgccg ctggttgcgc ttggcttgac cgacttgatc agcggccgct cgatttaaat    6600
ctcgagaggc ctgacgtcgg gcccggtacc a                                   6631

<210> SEQ ID NO 20
<211> LENGTH: 5863
<212> TYPE: DNA
<213> ORGANISM: Artificial Sequence
<220> FEATURE:
<223> OTHER INFORMATION: Plasmid

<400> SEQUENCE: 20
tcgagaggcc tgacgtcggg cccggtacca cgcgtcatat gcaggtgagg taaccccaaa      60
agaggtaaaa cccgcgccac cgacttttca ggagcgggga cgcgggtttt tgccatgaat     120
ccgaagatac tacatcagat ttttaggcca acttgagggc tgcgcgaagt tcatcaacgc     180
ggtcgatagc ctcccaagga aggtccaaat cagtgcgacc aaagtggccg taggcagcag     240
tgtcagcgta gatcggacga agcagatcaa gctcacggat aattgctgct ggacgcaggt     300
caaagacctc caacacggca gcctgaatct gctcgtcgct caggccttcc ttgttggtgt     360
caaaggtttc aacgtaaagt ccgactggct ttgcgcgtcc aatggcgtat gcaacctgaa     420
cttcagcgcg atcagcaagg cctgctgcca cgatgttctt tgctacccaa cgcatggcgt     480
atgcagcaga gcggtccacc ttgcttggat ccttaccgga gaatgctcca ccaccatggc     540
gagccatgcc accgtaggta tccacgatga tcttgcggcc ggtcagaccc gcatcaccca     600
tggggccacc cagaatgaag gaacctgaag ggttgatcaa cacggtgatc tcaccggttg     660
ccagatcctc aatgcctgcg tctttgatta cccaatcaat gacgtgttcg cgcagttggg     720
tttccaacca tgcacggtca acttctgggt cgtgctgggg ggagatgaca acggtatcca     780
ggtggctagg gcggtcttgc gcatcgtatg cgaaggtgac ctgggttttt ccgtctggac     840
gcaggtgagg aacgatgccc tctttacgaa cctgggtcag acgacgtgac agtcggtgcg     900
```

```
ccaacgcgat aggaagaggc atgtactctt cggtttcgtt ggtggcgtag ccgaacatca     960
ggccctggtc gccagcacct gcgcggtcgt cttcttcaac gtcgccgttg gtgcgggctt    1020
cgtcggagtt atccacgccg tcagcgattt cctgggactg ctcaccgatg gatactgaga    1080
cgccagcggt gcgtccgtcg aatccaacct cagaggagtt gaatccgatt tcgatgagct    1140
tgttgcggac taattgaggg atctctacgt aagcgctggt acggacctcg ccaacaacat    1200
ggacgattcc ggtggtgacc acagtttcca ctgcgacgcg cgactgcgga tcttttcga     1260
gcagcgcgtc caaatggta tcggaaatag catcacatat tttgtctgga tgtccctcag     1320
ttacagattc actggtgaac aaacggacgg cggttggctg agccacaaat acccttcttt    1380
cgaagaagtt gagaataaat agtcttaaat acaaaaaacc aatatagacc aagctgtcta    1440
aaactgcaat gtcagtggtc tagctggatt tttctagact tcgcgatacg ccagtgccgc    1500
gtcccaaatt tgcgcagcaa cctcgatttt gctgccgtgc tccacatcga ctaccccacc    1560
gtgagcatcc aaaatccagc cctcattgtg cttttgccca acactttgc ccatgcccac     1620
ctcattacac atgaggaggt cgcagccctt cttcccggga tttaaatcgc tagcgggctg    1680
ctaaaggaag cggaacacgt agaaagccag tccgcagaaa cggtgctgac cccggatgaa    1740
tgtcagctac tgggctatct ggacaaggga aaacgcaagc gcaaagagaa agcaggtagc    1800
ttgcagtggg cttacatggc gatagctaga ctgggcggtt ttatgacag caagcgaacc     1860
ggaattgcca gctggggcgc cctctggtaa ggttgggaag ccctgcaaag taaactggat    1920
ggctttcttg ccgccaagga tctgatgcg caggggatca agatctgatc aagagacagg     1980
atgaggatcg tttcgcatga ttgaacaaga tggattgcac gcaggttctc cggccgcttg    2040
ggtgcagagg ctattcggct atgactgggc acaacagaca atcggctgct ctgatgccgc    2100
cgtgttccgg ctgtcagcgc aggggcgccc ggttcttttt gtcaagaccg acctgtccgg    2160
tgccctgaat gaactgcagg acgaggcagc gcggctatcg tggctggcca cgacgggcgt    2220
tccttgcgca gctgtgctcg acgttgtcac tgaagcggga agggactggc tgctattggg    2280
cgaagtgccg gggcaggatc tcctgtcatc tcaccttgct cctgccgaga agtatccat     2340
catggctgat gcaatgcggc ggctgcatac gcttgatccg gctacctgcc cattcgacca    2400
ccaagcgaaa catcgcatcg agcgagcacg tactcggatg aagccggtc ttgtcgatca     2460
ggatgatctg gacgaagagc atcaggggct cgcgccagcc gaactgttcg ccaggctcaa    2520
ggcgcgcatg cccgacggcg aggatctcgt cgtgacccat ggcgatgcct gcttgccgaa    2580
tatcatggtg gaaaatggcc gcttttctgg attcatcgac tgtggccggc tgggtgtggc    2640
ggaccgctat caggacatag cgttggctac ccgtgatatt gctgaagagc ttggcggcga    2700
atgggctgac cgcttcctcg tgctttacgg tatcgccgct cccgattcgc agcgcatcgc    2760
cttctatcgc cttcttgacg agttcttctg agcgggactc tggggttcga atgaccgac     2820
caagcgacgc ccaacctgcc atcacgagat ttcgattcca ccgccgcctt ctatgaaagg    2880
ttgggcttcg gaatcgtttt ccgggacgcc ggctggatga tcctccagcg cggggatctc    2940
atgctggagt tcttcgccca cgctagcggc gcgccggcg gccggtgtg aaataccgca      3000
cagatgcgta aggagaaaat accgcatcag gcgctcttcc gcttcctcgc tcactgactc    3060
gctgcgctcg tcgttcggc tgcggcgagc ggtatcagct cactcaaagg cggtaatacg     3120
gttatccaca gaatcagggg ataacgcagg aaagaacatg tgagcaaaag gccagcaaaa    3180
ggccaggaac cgtaaaaagg ccgcgttgct ggcgtttttc cataggctcc gcccccctga    3240
cgagcatcac aaaaatcgac gctcaagtca gaggtggcga aacccgacag gactataaag    3300
```

-continued

```
ataccaggcg tttcccctg gaagctccct cgtgcgctct cctgttccga ccctgccgct      3360
taccggatac ctgtccgcct ttctcccttc gggaagcgtg gcgctttctc atagctcacg      3420
ctgtaggtat ctcagttcgg tgtaggtcgt tcgctccaag ctgggctgtg tgcacgaacc      3480
ccccgttcag cccgaccgct gcgccttatc cggtaactat cgtcttgagt ccaacccggt      3540
aagacacgac ttatcgccac tggcagcagc cactggtaac aggattagca gagcgaggta      3600
tgtaggcggt gctacagagt tcttgaagtg gtggcctaac tacggctaca ctagaaggac      3660
agtatttggt atctgcgctc tgctgaagcc agttaccttc ggaaaaagag ttggtagctc      3720
ttgatccggc aaacaaacca ccgctggtag cggtggtttt tttgtttgca agcagcagat      3780
tacgcgcaga aaaaaaggat ctcaagaaga tcctttgatc ttttctacgg ggtctgacgc      3840
tcagtggaac gaaaactcac gttaagggat tttggtcatg agattatcaa aaaggatctt      3900
cacctagatc cttttaaagg ccggccgcgg ccgccatcgg catttctttt tgcgttttta      3960
tttgttaact gttaattgtc cttgttcaag gatgctgtct ttgacaacag atgttttctt      4020
gcctttgatg ttcagcagga agctcggcgc aaacgttgat tgtttgtctg cgtagaatcc      4080
tctgtttgtc atatagcttg taatcacgac attgttttcct ttcgcttgag gtacagcgaa      4140
gtgtgagtaa gtaaaggtta catcgttagg atcaagatcc atttttaaca caaggccagt      4200
tttgttcagc ggcttgtatg ggccagttaa agaattagaa acataaccaa gcatgtaaat      4260
atcgttagac gtaatgccgt caatcgtcat ttttgatccg cgggagtcag tgaacaggta      4320
ccatttgccg ttcattttaa agacgttcgc gcgttcaatt tcatctgtta ctgtgttaga      4380
tgcaatcagc ggtttcatca ctttttttcag tgtgtaatca tcgtttagct caatcatacc      4440
gagagcgccg tttgctaact cagccgtgcg tttttttatcg ctttgcagaa gttttttgact      4500 ttcttgacgg aagaatgatg tgcttttgcc atagtatgct tgttaaata aagattcttc       4560 gccttggtag ccatcttcag ttccagtgtt tgcttcaaat actaagtatt tgtggccttt      4620
atcttctacg tagtgaggat ctctcagcgt atggttgtcg cctgagctgt agttgccttc      4680
atcgatgaac tgctgtacat tttgatacgt ttttccgtca ccgtcaaaga ttgatttata      4740
atcctctaca ccgttgatgt tcaaagagct gtctgatgct gatacgttaa cttgtgcagt      4800
tgtcagtgtt tgtttgccgt aatgtttacc ggagaaatca gtgtagaata aacgatttt      4860 tccgtcagat gtaaatgtgg ctgaacctga ccattcttgt gtttggtctt ttaggataga      4920
atcatttgca tcgaatttgt cgctgtcttt aaagacgcgg ccagcgtttt tccagctgtc      4980
aatagaagtt tcgccgactt tttgatagaa catgtaaatc gatgtgtcat ccgcatttt       5040 aggatctccg gctaatgcaa agacgatgtg gtagccgtga tagtttgcga cagtgccgtc      5100
agcgttttgt aatggccagc tgtcccaaac gtccaggcct tttgcagaag agatatttt       5160 aattgtggac gaatcaaatt cagaaacttg atatttttca ttttttttgct gttcagggat      5220 ttgcagcata tcatggcgtg taatatggga aatgccgtat gtttccttat atggcttttg      5280
gttcgtttct ttcgcaaacg cttgagttgc gcctcctgcc agcagtgcgg tagtaaaggt      5340
taatactgtt gcttgttttg caaacttttt gatgttcatc gttcatgtct ccttttttat      5400
gtactgtgtt agcggtctgc ttcttccagc cctcctgttt gaagatggca agttagttac      5460
gcacaataaa aaaagaccta aaatatgtaa ggggtgacgc caaagtatac actttgccct      5520
ttacacattt taggtcttgc ctgctttatc agtaacaaac ccgcgcgatt tacttttcga      5580
cctcattcta ttagactctc gtttggattg caactggtct atttttcctct tttgtttgat      5640
```

```
agaaaatcat aaaaggattt gcagactacg ggcctaaaga actaaaaaat ctatctgttt      5700
cttttcattc tctgtatttt ttatagtttc tgttgcatgg gcataaagtt gccttttttaa    5760 tcacaattca gaaatatca taatatctca tttcactaaa taatagtgaa cggcaggtat      5820
atgtgatggg ttaaaaagga tcggcggccg ctcgatttaa atc                       5863
```

<210> SEQ ID NO 21
<211> LENGTH: 1224
<212> TYPE: DNA
<213> ORGANISM: Artificial Sequence
<220> FEATURE:
<223> OTHER INFORMATION: Plasmid
<220> FEATURE:
<221> NAME/KEY: CDS
<222> LOCATION: (1)..(1224)
<223> OTHER INFORMATION:

<400> SEQUENCE: 21

```
gtg gct cag cca acc gcc gtc cgt ttg ttc acc agt gaa tct gta act       48
Val Ala Gln Pro Thr Ala Val Arg Leu Phe Thr Ser Glu Ser Val Thr
1               5                   10                  15 gag gga cat cca gac aaa ata tgt gat gct att tcc gat acc att ttg       96
Glu Gly His Pro Asp Lys Ile Cys Asp Ala Ile Ser Asp Thr Ile Leu
        20                  25                  30 gac gcg ctg ctc gaa aaa gat ccg cag tcg cgc gtc gca gtg gaa act      144
Asp Ala Leu Leu Glu Lys Asp Pro Gln Ser Arg Val Ala Val Glu Thr
    35                  40                  45 gtg gtc acc acc gga atc gtc cat gtt gtt ggc gag gtc cgt acc agc      192
Val Val Thr Thr Gly Ile Val His Val Val Gly Glu Val Arg Thr Ser
50                  55                  60 gct tac gta gag atc cct caa tta gtc cgc aac aag ctc atc gaa atc      240
Ala Tyr Val Glu Ile Pro Gln Leu Val Arg Asn Lys Leu Ile Glu Ile
65                  70                  75                  80 gga ttc aac tcc tct gag gtt gga ttc gac gga cgc acc gct ggc gtc      288
Gly Phe Asn Ser Ser Glu Val Gly Phe Asp Gly Arg Thr Ala Gly Val
                85                  90                  95 tca gta tcc atc ggt gag cag tcc cag gaa atc gct gac ggc gtg gat      336
Ser Val Ser Ile Gly Glu Gln Ser Gln Glu Ile Ala Asp Gly Val Asp
            100                 105                 110 aac tcc gac gaa gcc cgc acc aac ggc gac gtt gaa gaa gac gac cgc      384
Asn Ser Asp Glu Ala Arg Thr Asn Gly Asp Val Glu Glu Asp Asp Arg
        115                 120                 125 gca ggt gct ggc gac cag ggc ctg atg ttc ggc tac gcc acc aac gaa      432
Ala Gly Ala Gly Asp Gln Gly Leu Met Phe Gly Tyr Ala Thr Asn Glu
    130                 135                 140 acc gaa gag tac atg cct ctt cct atc gcg ttg gcg cac cga ctg tca      480
Thr Glu Glu Tyr Met Pro Leu Pro Ile Ala Leu Ala His Arg Leu Ser
145                 150                 155                 160 cgt cgt ctg acc cag gtt cgt aaa gag ggc atc gtt cct cac ctg cgt      528
Arg Arg Leu Thr Gln Val Arg Lys Glu Gly Ile Val Pro His Leu Arg
                165                 170                 175 cca gac gga aaa acc cag gtc acc ttc gca tac gat gcg caa gac cgc      576
Pro Asp Gly Lys Thr Gln Val Thr Phe Ala Tyr Asp Ala Gln Asp Arg
            180                 185                 190 cct agc cac ctg gat acc gtt gtc atc tcc acc cag cac gac cca gaa      624
Pro Ser His Leu Asp Thr Val Val Ile Ser Thr Gln His Asp Pro Glu
        195                 200                 205 gtt gac cgt gca tgg ttg gaa acc caa ctg cgc gaa cac gtc att gat      672
Val Asp Arg Ala Trp Leu Glu Thr Gln Leu Arg Glu His Val Ile Asp
    210                 215                 220 tgg gta atc aaa gac gca ggc att gag gat ctg gca acc ggt gag atc      720
Trp Val Ile Lys Asp Ala Gly Ile Glu Asp Leu Ala Thr Gly Glu Ile
```

```
Trp Val Ile Lys Asp Ala Gly Ile Glu Asp Leu Ala Thr Gly Glu Ile
225                 230                 235                 240 acc gtg ttg atc aac cct tca ggt tcc ttc att ctg ggt ggc ccc atg      768
Thr Val Leu Ile Asn Pro Ser Gly Ser Phe Ile Leu Gly Gly Pro Met
245                 250                 255 ggt gat gcg ggt ctg acc ggc cgc aag atc atc gtg gat acc tac ggt      816
Gly Asp Ala Gly Leu Thr Gly Arg Lys Ile Ile Val Asp Thr Tyr Gly
260                 265                 270 ggc atg gct cgc cat ggt ggt gga gca ttc tcc ggt aag gat cca agc      864
Gly Met Ala Arg His Gly Gly Gly Ala Phe Ser Gly Lys Asp Pro Ser
275                 280                 285 aag gtg gac cgc tct gct gca tac gcc atg cgt tgg gta gca aag aac      912
Lys Val Asp Arg Ser Ala Ala Tyr Ala Met Arg Trp Val Ala Lys Asn
290                 295                 300 atc gtg gca gca ggc ctt gct gat cgc gct gaa gtt cag gtt gca tac      960
Ile Val Ala Ala Gly Leu Ala Asp Arg Ala Glu Val Gln Val Ala Tyr
305                 310                 315                 320 gcc att gga cgc gca aag cca gtc gga ctt tac gtt gaa acc ttt gac     1008
Ala Ile Gly Arg Ala Lys Pro Val Gly Leu Tyr Val Glu Thr Phe Asp
325                 330                 335 acc aac aag gaa ggc ctg agc gac gag cag att cag gct gcc gtg ttg     1056
Thr Asn Lys Glu Gly Leu Ser Asp Glu Gln Ile Gln Ala Ala Val Leu
340                 345                 350 gag gtc ttt gac ctg cgt cca gca gca att atc cgt gag ctt gat ctg     1104
Glu Val Phe Asp Leu Arg Pro Ala Ala Ile Ile Arg Glu Leu Asp Leu
355                 360                 365 ctt cgt ccg atc tac gct gac act gcc tac ggc cac ttt ggt cgc         1152
Leu Arg Pro Ile Tyr Ala Asp Thr Ala Ala Tyr Gly His Phe Gly Arg
370                 375                 380 act gat ttg gac ctt cct tgg gag gct atc gac cgc gtt gat gaa ctt     1200
Thr Asp Leu Asp Leu Pro Trp Glu Ala Ile Asp Arg Val Asp Glu Leu
385                 390                 395                 400 cgc gca gcc ctc aag ttg gcc taa                                     1224
Arg Ala Ala Leu Lys Leu Ala
405

<210> SEQ ID NO 22
<211> LENGTH: 407
<212> TYPE: PRT
<213> ORGANISM: Artificial Sequence
<220> FEATURE:
<223> OTHER INFORMATION: Plasmid

<400> SEQUENCE: 22

Val Ala Gln Pro Thr Ala Val Arg Leu Phe Thr Ser Glu Ser Val Thr
1               5                   10                  15

Glu Gly His Pro Asp Lys Ile Cys Asp Ala Ile Ser Asp Thr Ile Leu
            20                  25                  30

Asp Ala Leu Leu Glu Lys Asp Pro Gln Ser Arg Val Ala Val Glu Thr
        35                  40                  45

Val Val Thr Thr Gly Ile Val His Val Gly Glu Val Arg Thr Ser
    50                  55                  60

Ala Tyr Val Glu Ile Pro Gln Leu Val Arg Asn Lys Leu Ile Glu Ile
65                  70                  75                  80

Gly Phe Asn Ser Ser Glu Val Gly Phe Asp Gly Arg Thr Ala Gly Val
            85                  90                  95

Ser Val Ser Ile Gly Glu Gln Ser Gln Glu Ile Ala Asp Gly Val Asp
        100                 105                 110

Asn Ser Asp Glu Ala Arg Thr Asn Gly Asp Val Glu Glu Asp Asp Arg
```

```
            115                 120                 125
Ala Gly Ala Gly Asp Gln Gly Leu Met Phe Gly Tyr Ala Thr Asn Glu
130                 135                 140

Thr Glu Glu Tyr Met Pro Leu Pro Ile Ala Leu Ala His Arg Leu Ser
145                 150                 155                 160

Arg Arg Leu Thr Gln Val Arg Lys Glu Gly Ile Val Pro His Leu Arg
165                 170                 175

Pro Asp Gly Lys Thr Gln Val Thr Phe Ala Tyr Asp Ala Gln Asp Arg
180                 185                 190

Pro Ser His Leu Asp Thr Val Val Ile Ser Thr Gln His Asp Pro Glu
195                 200                 205

Val Asp Arg Ala Trp Leu Glu Thr Gln Leu Arg Glu His Val Ile Asp
210                 215                 220

Trp Val Ile Lys Asp Ala Gly Ile Glu Asp Leu Ala Thr Gly Glu Ile
225                 230                 235                 240

Thr Val Leu Ile Asn Pro Ser Gly Ser Phe Ile Leu Gly Gly Pro Met
245                 250                 255

Gly Asp Ala Gly Leu Thr Gly Arg Lys Ile Ile Val Asp Thr Tyr Gly
260                 265                 270

Gly Met Ala Arg His Gly Gly Gly Ala Phe Ser Gly Lys Asp Pro Ser
275                 280                 285

Lys Val Asp Arg Ser Ala Ala Tyr Ala Met Arg Trp Val Ala Lys Asn
290                 295                 300

Ile Val Ala Ala Gly Leu Ala Asp Arg Ala Glu Val Gln Val Ala Tyr
305                 310                 315                 320

Ala Ile Gly Arg Ala Lys Pro Val Gly Leu Tyr Val Glu Thr Phe Asp
325                 330                 335

Thr Asn Lys Glu Gly Leu Ser Asp Glu Gln Ile Gln Ala Ala Val Leu
340                 345                 350

Glu Val Phe Asp Leu Arg Pro Ala Ala Ile Ile Arg Glu Leu Asp Leu
355                 360                 365

Leu Arg Pro Ile Tyr Ala Asp Thr Ala Ala Tyr Gly His Phe Gly Arg
370                 375                 380

Thr Asp Leu Asp Leu Pro Trp Glu Ala Ile Asp Arg Val Asp Glu Leu
385                 390                 395                 400

Arg Ala Ala Leu Lys Leu Ala
405

<210> SEQ ID NO 23
<211> LENGTH: 9
<212> TYPE: PRT
<213> ORGANISM: Artificial Sequence
<220> FEATURE:
<223> OTHER INFORMATION: variable partial sequence
<220> FEATURE:
<221> NAME/KEY: MISC_FEATURE
<222> LOCATION: (2)..(2)
<223> OTHER INFORMATION: Xaa=Phe or Tyr
<220> FEATURE:
<221> NAME/KEY: MISC_FEATURE
<222> LOCATION: (3)..(3)
<223> OTHER INFORMATION: Xaa=Asp or Ser
<220> FEATURE:
<221> NAME/KEY: MISC_FEATURE
<222> LOCATION: (4)..(4)
<223> OTHER INFORMATION: Xaa=any amino acid
<220> FEATURE:
<221> NAME/KEY: MISC_FEATURE
<222> LOCATION: (5)..(5)
<223> OTHER INFORMATION: Xaa=any amino acid
```

```
-continued

<220> FEATURE:
<221> NAME/KEY: MISC_FEATURE
<222> LOCATION: (7)..(7)
<223> OTHER INFORMATION: Xaa=amino acid other than Cys
<220> FEATURE:
<221> NAME/KEY: MISC_FEATURE
<222> LOCATION: (6)..(6)
<223> OTHER INFORMATION: Xaa=Ser or Thr
<220> FEATURE:
<221> NAME/KEY: MISC_FEATURE
<222> LOCATION: (8)..(8)
<223> OTHER INFORMATION: Xaa=Gly or Ala

<400> SEQUENCE: 23

Gly Xaa Xaa Xaa Xaa Xaa Xaa Xaa Val
1               5
```

METHOD FOR THE PRODUCTION OF SULPHER-CONTAINING FINE CHEMICALS BY FERMENTATION

The invention relates to a novel method for the production by fermentation of sulfur-containing fine chemicals, in particular L-methionine and L-cysteine, which makes use of bacteria in which nucleotide sequences encoding mutants of S-adenosylmethionine synthase (metK) (E.C.2.5.1.6) are expressed; to nucleotide sequences which encode these mutants, to the recombinant microorganisms transformed therewith, and to novel metK mutants with modified enzyme activity.

PRIOR ART

Sulfur-containing fine chemicals such as, for example, methionine, homocysteine, S-adenosylmethionine, glutathione, cysteine, biotin, thiamine and liponic acid, are produced in cells via natural metabolic processes and used in a large number of industries including the food, feed, cosmetics and pharmaceutical industries. These substances, which are referred to generically as "sulfur-containing fine chemicals", encompass organic acids, proteinogenic and nonproteinogenic amino acids, vitamins and cofactors. Most expediently they are produced on an industrial scale by growing bacteria which have been developed for producing and secreting large amounts of the desired substance in question. Organisms which are particularly suitable for this purpose are the Gram-positive, nonpathogenic coryneform bacteria.

It is known that amino acids are produced by fermenting strains of coryneform bacteria, in particular *Corynebacterium glutamicum*. Owing to their high importance, the production methods are constantly being improved. Improvements with regard to the production methods may relate to aspects of fermentation technology, such as, for example, stirring and nitrogen supply, or the composition of the nutrient media, such as, for example, the sugar concentration during fermentation, or downstream processing, for example by ion-exchange chromatography, or the intrinsic performance parameters of the microorganism itself.

Strain selection has given rise to a series of mutant strains which produce a group of desirable compounds from the series of the sulfur-containing fine chemicals. Methods applied for improving the performance parameters of these microorganisms with regard to the production of a particular molecule are mutagenesis, selection and choice of mutants. However, this is a time-consuming and difficult procedure. In this manner, strains are obtained which are, for example, resistant to antimetabolites, such as, for example, to the methionine analogs a-methylmethionine, ethionine, norleucin, N-acetylnorleucine, S-trifluoromethylhomocysteine, 2-amino-5-heptenoic acid, selenomethionine, methionine sulfoximine, methoxine or 1-aminocyclopentanecarboxylic acid, or which are auxotrophic with regard to metabolites of regulatory importance and which produce sulfur-containing fine chemicals, such as, for example, L-methionine.

Methods of recombinant DNA technology have also been employed for some years for the strain improvement of L-amino-acid-producing *Corynebacterium* strains, in which individual amino acid biosynthesis genes are amplified and the effect on the amino acid production is studied.

JP-A-06-020809 discloses a nucleotide sequence for a gene from *Brevibacterium flavum* MJ-233, a coryneform bacterial, which encodes S-adenosylmethionine. The corresponding amino acid sequence encompasses 412 amino acids. In each of positions 24 and 94, inter alia, which are conserved in the corresponding enzymes of a large number of other coryneform bacteria, the protein has a cysteine residue. The amino acid sequence disclosed has a characteristic sequence segment between residues 137 and 154. The generation of mutants and their use in the production by fermentation of sulfur-containing fine chemicals is not described therein.

WO-A-01/00843 discloses a metK gene from *C. glutamicum*, which encodes a protein with 407 amino acids and has a sequence as shown in SEQ ID NO:16.

As a rule, improvements in the production by fermentation of fine chemicals correlate with improved substance fluxes and yields. It is important to prevent, or to reduce, intermediate inhibition or end-product inhibition of enzymes which are important for the synthesis. The prevention or reduction of diversions of the carbon flux toward undesired products or byproducts is likewise advantageous.

The effect of metabolites on the enzymatic activities of metabolic enzymes can be studied. Examples of such enzymes can be meta, metB, metC, MetY, metH, metE, metF and other enzymes in the metabolism of microorganisms. An important metabolite of methionine, and thus an important diversion, is S-adenosylmethionine.

However, S-adenosylmethionine is simultaneously also a crucial regulator of methoinine biosynthesis. For example, it is known that the biosynthesis of L-methione in *E. coli* is inhibited by S-adenosylmethionine. In this system, S-adenosylmethionine acts as a corepressor of the repressor metJ (Weissbach, H. Brot, N. (1991) Mol Microbiol. 5 (7), 1593-1597).

At the same time, the synthesis of S-adenosylmethionine is an important diversion from the desired product of interest, L-methionine. Reducing the amount of S-adenosylmethionine formed is therefore desirable for several reasons, namely:

a) the amount of L-methionine formed would be increased, b) the repression of genes of methionine biosynthesis would be reduced, and c) the feedback inhibition of enzymes of methionine biosynthesis would be reduced.

Deletion of the metK gene would be the simplest way of preventing the formation of S-adenosylmethionine. In Wei, Y. and Newman, E. B. (2002) Mol. Microbiol. 43 (6), 1651-1656, however, metK is described as an essential gene and thus appears to the skilled worker as a starting point for the improved production by fermentation of sulfur-containing fine chemicals, in particular L-methionine.

SUMMARY OF THE INVENTION

It is an object of the present invention to provide a novel method for the improved production by fermentation of sulfur-containing fine chemicals, in particular L-methionine, and the means required therefore.

Surprisingly, it has been found that this object is achieved by providing a method for the production by fermentation of a sulfur-containing fine chemical which comprises the expression of a metK nucleotide sequence in a coryneform bacterium, the nucleotide sequence encoding an S-adenosylmethionine synthase mutant whose activity is modified, preferably reduced, over the wild-type enzyme. For example, the S-adenosylmethionine synthase mutant is derived from *Corynebacterium glutamicum* and, measured in *Corynebacterium glutamicum*, shows less activity than the wild-type enzyme.

A first subject matter of the invention relates to a method for the production by fermentation of at least one sulfur-containing fine chemical, which comprises the following steps:
a) fermentation of a coryneform bacterial culture which produces the desired sulfur-containing fine chemical, the coryneform bacteria expressing at least one nucleotide sequence which encodes a protein with modified S-adenosylmethionine synthase (metK) activity;
b) enrichment of the sulfur-containing fine chemical in the medium and/or in the bacterial cells, and
c) isolation of the sulfur-containing fine chemical, which preferably comprises L-methionine.

In accordance with a preferred embodiment, the mutated coryneform bacterium additionally has an improved metY activity and/or an increased L-methionine amount in comparison with the unmutated wild type (for example expressed in g/l fermentation liquor).

The metK-encoding sequence which is used in particular in the method according to the invention is a coding nucleotide sequence which encodes a protein with reduced metK activity in which at least one cysteine residue of the wild-type protein is substituted.

Preferably, the metK-encoding sequence is a coding nucleotide sequence which encodes a protein with metK activity which has the following amino acid part-sequence as shown in SEQ ID NO:23:

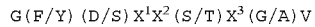

where
X$^1$ and X$^2$ independently of one another represent any amino acid;
and
X$^3$ represents an amino acid other than Cys.

Especially preferred is a method in accordance with the above definition in which the metK-encoding sequence encodes a protein with metK activity, the protein encompassing an amino acid sequence from Val1 to Ala407 as shown in SEQ ID NO: 22 or an amino acid sequence which is homologous thereto and which represents a protein with functional equivalence.

The metK-encoding sequence employed in accordance with the invention preferably comprises a coding sequence as shown in SEQ ID NO: 21 or a nucleotide sequence which is homologous thereto and which encodes a protein with metK activity.

The coding metK sequence is preferably a DNA which is capable of replication in coryneform bacteria or stably integrated into the chromosome, or an RNA.

In accordance with a preferred embodiment, the method according to the invention is carried out by
a) using a bacterial strain which has been transformed with a plasmid vector and which carries at least one copy of the coding metK sequence under the control of regulatory sequences, or
b) using a strain in which the coding metK sequence has been integrated into the bacterial chromosome.

Especially preferred are strains as defined above in which, additionally, all or some of the activity of the metK wild type enzyme has been removed, such as, for example, by deletion of the coding sequence of the wild-type enzyme.

Moreover, it may be desirable to ferment bacteria in which additionally at least one further gene of the biosynthetic pathway of the desired sulfur-containing fine chemical is enhanced and/or in which at least one metabolic pathway which reduces the formation of the desired sulfur-containing fine chemical is at least partly eliminated.

This is why, in accordance with a further embodiment of the method according to the invention, coryneform bacteria in which at least one of the genes selected from among
1) the gene lysC, which encodes an aspartate kinase,
2) the gene asd, which encodes an aspartate-semialdehyde dehydrogenase,
3) the gene gap, which encodes glycerinaldehyde-3-phosphate dehydrogenase,
4) the gene pgk, which encodes 3-phosphoglycerate kinase,
5) the gene pyc, which encodes pyruvate carboxylase,
6) the gene tpi, which encodes triose-phosphate isomerase,
7) the gene meta, which encodes homoserine O-acetyltransferase,
8) the gene metB, which encodes cystathionine-gamma synthase,
9) the gene metC, which encodes cystathionine-gamma lyase,
10) the gene metH, which encodes methionine synthase,
11) the gene glyA, which encodes serine hydroxymethyltransferase,
12) the gene metY, which encodes O-acetylhomoserine sulfhydrylase,
13) the gene metF, which encodes methylenetetrahydrofolate reductase,
14) the gene serC, which encodes phosphoserine aminotransferase,
15) the gene serB, which encodes phosphoserine phosphatase,
16) the gene cysE, which encodes serine acetyltransferase,
17) the gene cysk, which encodes cysteine synthase,
18) the gene hom, which encodes homoserine dehydrogenase, is simultaneously overexpressed, are fermented.

In accordance with another embodiment of the method according to the invention, coryneform bacteria are fermented in which at least one of the genes selected among genes of the abovementioned groups 1) to 18) is simultaneously mutated in such a way that the activity of the corresponding proteins influenced to a lesser degree in comparison with unmutated proteins, or unaffected by metabolites and that in particular the production according to the invention of the fine chemical is not adversely affected, or in such a way that their specific enzyme activity is increased.

In accordance with another embodiment of the method according to the invention coryneform bacteria are fermented in which simultaneously at least one of the genes selected from among
19) the gene thrB, which encodes homoserine kinase,
20) the gene ilvA, which encodes threonine dehydratase,
21) the gene thrC, which encodes threonine synthase,
22) the gene ddh, which encodes meso-diaminopimelate D dehydrogenase,
23) the gene pck, which encodes phosphoenol-pyruvate carboxykinase,
24) the gene pgi, which encodes glucose-6-phosphate-6 isomerase,
25) the gene poxB, which encodes pyruvate oxidase,
26) the gene dapA, which encodes dihydrodipicolinate synthase,
27) the gene dapB, which encodes dihydrodipicolinate reductase, or
28) the gene lysA, which encodes diaminopicolinate decarboxylase, is attenuated, in particular by reducing the expression rate of the corresponding gene.

In accordance with another embodiment of the method according to the invention, coryneform bacteria are fermented in which at least one of the genes of the above groups 19) to 28) is simultaneously mutated in such a way that the enzyme activity of the corresponding protein is reduced in part or fully.

Microorganisms which are preferably used in the method according to the invention are those of the species *Corynebacterium glutamicum*.

The invention furthermore relates to a method for producing an L-methionine-containing animal feed additive from fermentation broths, which comprises the following steps:
- a) culturing and fermentation of an L-methionine-producing microorganism, preferably with a reduced metK activity in accordance with the above definition, in a fermentation medium,
- b) removal of water from the L-methionine-containing fermentation broth;
- c) removal of from 0 to 100% by weight of the biomass formed during fermentation; and
- d) drying of the fermentation broth obtained according to b) and/or c), in order to obtain the animal feed additive in the desired powder or granule form.

The invention furthermore relates to isolated polynucleotides which encode a polypeptide with reduced metK activity in accordance with the above definition, and to metK mutants with reduced activity which are encoded by these polynucleotides.

Furthermore, the invention relates to recombinant coryneform bacteria which express a mutated metK gene in accordance with the above definition, in particular those recombinant coryneform bacteria which no longer express the metK wild-type enzyme.

In comparison with the corresponding wild-type strain, preferred recombinant coryneform bacteria show at least one of the following traits:
- a) lower intracellular S-adenosylmethionine titer
- b) lower intracellular S-adenosylmethionine synthase concentration, or
- c) lower S-adenosylmethionine synthase activity, determined with reference to the rate of S-adenosylmethionine formation, and additionally if appropriate at least one of the following traits:
- d) improved metY activity or
- e) increased amount of L-methionine.

DETAILED DESCRIPTION OF THE INVENTION a) General Terms

The term proteins with the biological activity of "S-adenosylmethionine synthase", also abbreviated to metK (E.C.2.5.1.6) refers to those proteins which are capable of converting L-methionine and ATP into S-adenosylmethionine. The skilled worker is familiar with other details of the metK protein. The enzyme activity of metK can be detected by enzyme assays, protocols for which are found in: Markham, G. D. et al. (1983) Methods in Enzymology 94:219-222.

Within the scope of the present invention, the term "sulfur-containing fine chemical" encompasses any chemical compound which contains at least one sulfur atom bonded covalently and which can be obtained by a fermentation method according to the invention. Nonlimiting examples are methionine, homocysteine, S-adenosylmethionine, cysteine and in particular methionine and S-adenosylmethionine.

Within the scope of the present invention, the terms "L-methionine", "methionine", "homocysteine" and "S-adenosylmethionine" also encompass the corresponding salts such as, for example, methionine-hydrochloride or methionine sulfate.

"Polynucleotides" generally refers to polyribonucleotides (RNA) and polydeoxyribonucleo-tides (DNA), which may take the form of unmodified RNA or DNA or modified RNA or DNA.

"Polypeptides" are understood as meaning, in accordance with the invention, peptides or proteins comprising two or more amino acids which are bonded via peptide bonds.

The term "metabolite" refers to chemical compounds which occur in the metabolism of organisms as intermediates or else end products and which, besides their property as chemical units, may also exert a modulatory effect on enzymes and their catalytic activity. It is known from the literature that such metabolites can have both an inhibitory and stimulatory effect on the activity of enzymes (Biochemistry, Stryer, Lubert, 1995 W. H. Freeman & Company, New York, N.Y.). The literature also describes that it is possible to produce, by measures such as mutating the genomic DNA by UV radiation, ionizing radiation or mutagenic substances and subsequently selecting for specific phenotypes, in organisms, those enzymes in which the influence by metabolites has been modified (Sahm H., Eggeling L., de Graaf A. A. Biological Chemistry 381(9-10):899-910, 2000; Eikmanns B J., Eggeling L., Sahm H. Antonie van Leeuwenhoek. 64:145-63, 1993-94). These modified properties can also be obtained by targeted measures. In this context, the skilled worker also knows to specifically modify, in genes for enzymes, specific nucleotides of the DNA which encodes the protein in such a manner that the protein resulting from the expressed DNA sequence has specific novel characteristics. For example, this may result in the modulating effect of metabolites being modified over the unmodified protein. Also, the activity of enzymes can be affected in such a way that a diminished reaction rate or a change in affinity to the substrate results.

In the context of the invention, the terms "express" or "enhancement" or "overexpression" in the context of the invention describe the production or increase of the intracellular activity of one or more enzymes in a microorganism which are encoded by the DNA in question. To this end, it is possible, for example, to introduce a gene into an organism, to replace an existing gene by another gene, to increase the copy number of the gene or genes, to use a strong promoter or to use a gene which encodes an enzyme in question with high activity; if appropriate, these measures can be combined.

Within the context of the invention, the terms "to attenuate" and "to reduce" describe the attenuation or reduction of the intracellular activity of one or more enzymes in a microorganism which are encoded by the DNA in question. To this end, it is possible, for example, to delete a gene in an organism, to replace an existing gene by another gene, to reduce the copy number of a transcript of the gene or genes, to use a weak promoter or to use a gene which encodes a corresponding enzyme with low activity; if appropriate, these measures can be combined.

The "reduced activity" of an S-adenosylmethionine synthase mutant according to the invention or of a functional equivalent can be determined by comparison with the activity of the native S-adenosylmethionine synthase, such as, for example, from *Corynebacterium glutamicum* wild type, ATCC 13032. To this end, plasmids which replicate in *Corynebacterium glutamicum* and which carry the genes for S-adenosylmethionine synthase mutants are suitably introduced by transformation into, for example, *Corynebacterium* glutamicum wild type, ATCC 13032. Moreover, suitable plasmids which express the wild-type enzyme S-adenosylmethionine synthase are introduced into *Corynebacterium glutamicum* wild type, ATCC 13032. *Corynebacterium glutamicum* transformants thus obtained are grown in suitable media and harvested during the logarithmic growth phase at the same $OD_{600}$. Thereafter, protein extracts are prepared from the harvested cells of the two transformants following known protocols. Identical amounts of these protein extracts (following protein identification) are then employed in an S-adenosylmethionine synthase assay by the method of Markham, G. D. et al. (1983) Methods in Enzymology 94: 219-222. The radioactivity of the S-adenosylmethionine formed is determined in a scintillation counter. Taking into consideration the specific activity of the radioactive L-methionine and the amount of protein employed, the rate of S-adenosylmethionine formation can be determined from the increase in incorporated radioactivity per unit time. It has the unit μmol S-adenosylmethionine/min*mg protein. This rate can be compared between wild-type enzyme and mutant enzyme. Starting from other wild-type enzymes with S-adenosylmethionine synthase activity, mutants which are useful in accordance with the invention can be generated by the same principle.

A "reduced activity" is present in accordance with the invention in particular when the specific activity of the mutant is reduced to a residual activity of approximately 1 to 90%, preferably 3 to 70%, such as, for example, 5 to 10% of the wild-type activity.

b) metK proteins according to the invention

The polynucleotide sequences according to the invention encode proteins with modified, in particular reduced, S-adenosylmethionine synthase activity as defined above.

The mutants which are useful according to the invention are preferably obtained by substituting one or more conserved cysteine residues within the metK amino acid sequence of Gram-positive and/or Gram-negative, or in particular coryneform, bacteria. Conserved cysteine residues can be identified readily with the aid of sequence alignments. Nonlimiting examples of conserved Cys residues in bacterial S-adenosylmethionine synthases are Cys24 and Cys94 of the enzyme from *C. glutamicum*, which are found in a multiplicity of bacteria.

In a preferred group of mutants according to the invention, Cys24 and/or Cys94 (according to *C. glutamicum* ATCC 13032 metK) are substituted by an amino acid other than Cys, preferably alanine, whereby the enzyme activity is reduced in the above manner.

"Functional equivalents" or analogs of the specifically disclosed polypeptides are, within the scope of the present invention, polypeptides which differ from them but which still retain the desired biological activity such as, for example, substrate specificity.

In accordance with the invention, "functional equivalents" are understood as meaning, in particular, mutants which have another amino acid than the amino acid which has been mentioned specifically in at least one of the abovementioned sequence positions, but which still retain one of the abovementioned biological activities. Thus, "functional equivalents" encompass the mutants obtainable by one or more amino acid additions, substitutions, deletions and/or inversions, it being possible for the abovementioned modifications to be located at any sequence position as long as they give rise to a mutant with the profile of characteristics according to the invention. In particular, functional equivalence also exists when the reactivity pattern between mutant and unmodified polypeptide agree in quality, i.e. for example when identical substrates are converted at different rates.

Naturally, "functional equivalents" also encompass polypeptides which can be obtained from other organisms, and naturally occurring variants. For example, ranges of homologous sequence regions can be identified by sequence, and equivalent enzymes can be determined with a view to the specific aims of the invention.

Likewise, "functional equivalents" encompass fragments, preferably individual domains or sequence motifs, or the polypeptides according to the invention which have for example the desired biological function.

Moreover, "functional equivalents" are fusion proteins with one of the abovementioned poly-peptide sequences or functional equivalents derived therefrom and at least one further, functionally different, heterologous sequence in functional N- or C-terminal linkage (i.e. without the fusion protein moieties being substantially adversely affected functionally by each other). Nonlimiting examples of such heterologous sequences are, for example, signal peptides, enzymes, immunoglobulins, surface antigens, receptors or receptor ligands.

"Functional equivalents" which are also encompassed in accordance with the invention are homologs to the specifically disclosed proteins. These homologs have at least 20%, 30%, or for example 40%, 50%, preferably at least approximately 60%, 65%, 70%, or 75%, in particular at least 85%, such as, for example, 90%, 95% or 99%, homology with one of the specifically disclosed sequences, calculated using Pearson and Lipman's algorithm, Proc. Natl. Acad, Sci. (USA) 85(8), 1988, 2444-2448.

Mutants and functional analogs which are especially preferred are those which contain the characteristic part-sequence

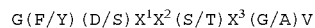

as defined above, where $X^3$ is an amino acid introduced by mutation other than Cys, in particular alanine. $X^3$ corresponds to Cys94 of the metK wild-type sequence of *C. glutamicum* (SEQ ID NO: 16). $X^2$ preferably represents Ala, Glu, Asp, Asn or Arg, and $X^1$ preferably represents Gly, Cys, Ser or Ala.

Homologs of the proteins or polypeptides according to the invention can be generated by mutagenesis, for example by point mutation or truncation of the protein. The term "homolog" as used in the present context relates to a variant form of the protein which acts as agonist or antagonist of the protein activity.

Homologs of the proteins according to the invention can be identified by screening combinatory libraries of mutants, such as, for example, truncated mutants. A variegated library of protein variants can be generated for example by combinatory mutagenesis at the nucleic acid level, such as, for example, by enzymatically ligating a mixture of synthetic oligonucleotides. A multiplicity of methods are available which can be used for generating libraries of potential homologs from a degenerate oligonucleotide sequence. The degenerate gene sequence can be synthesized chemically in a DNA synthesizer, and the synthetic gene can then be ligated into a suitable expression vector. The use of a set of degenerate genes makes it possible to provide, in a mixture, all sequences which encode the desired set of potential protein sequences. Methods for the synthesis of degenerate oligonucleotides are known to the skilled worker (for example Narang, S. A. (1983) Tetrahedron 39:3; Itakura et al. (1984)

Annu. Rev. Biochem. 53:323; Itakura et al., (1984) Science 198:1056; Ike et al. (1983) Nucleic Acids Res. 11:477).

Libraries of fragments of the protein codon may additionally be used for generating a variegated population of protein fragments for screening and subsequently selecting homologs of a protein according to the invention. In one embodiment, a library of coding sequence fragments can be generated by treating a double-stranded PCR fragment of a coding sequence with a nuclease under conditions under which nicking only takes place approximately once per molecule, denaturing the double-stranded DNA, renaturing the DNA with the formation of double-stranded DNA which may encompass sense/antisense pairs of various nicked products, removing single-stranded segments from newly-formed duplices by treatment with S1 nuclease, and ligating the resulting fragment library into an expression vector. This method allows an expression library which encodes N-terminal, C-terminal and internal fragments with various sizes of the protein according to the invention to be generated.

A plurality of techniques for the mutagenesis of genes are known in the prior art: Coco, W M et al. 2001. DNA shuffling method for generating highly recombined genes and evolved enzymes. Nature Biotechnol. 19:354-359; DE 19953854; Leung D W et al. 1989. A method for random mutagenesis of a defined DNA segment using a modified polymerase chain reaction. Technique 1:11-15; Stemmer WPC 1994. DNA shuffling by random fragmentation and reassembly: in vitro recombination for molecular evolution. Proc. Natl. Acad. Sci USA 91:10747-10751; and U.S. Pat. No. 5,811,238. These methods can be employed for generating mutants which are useful in accordance with the invention.

A plurality of techniques for screening gene products of combinatory libraries which have been generated by point mutations or truncation and for screening cDNA libraries for gene products with a selected characteristic are known in the prior art. These techniques can be adapted to rapid screening of the gene libraries which have been generated by combinatory mutagenesis of homologs according to the invention. Techniques which are most frequently used for screening large gene libraries which are subjected to high-throughput analysis include cloning the gene library into replicable expression vectors, transforming the suitable cells with the resulting vector library and expressing the combinatory genes under conditions under which the detection of the desired activity simplifies the isolation of the vector encoding the gene whose product has been detected. Recursive ensemble mutagenesis (REM), a technique which increases the frequency of functional mutants in the libraries, can be used in combination with the screening assays for identifying homologs (Arkin and Yourvan (1992) PNAS 89:7811-7815; Delgrave et al. (1993) Protein Engineering 6(3):327-331.

c) Polynucleotides According to the Invention

Likewise, the invention relates to nucleic acid sequences (single- and double-stranded DNA and RNA sequences such as, for example, cDNA and mRNA) encoding a metK enzyme according to the invention and its functional equivalents which can be obtained for example using synthetic nucleotide analogs, inter alia.

The invention relates both to isolated nucleic acid molecules which encode polypeptides or proteins according to the invention, or biologically active segments of these, and to nucleic acid fragments which can be used for example as hybridization probes or primers for identifying or amplifying coding nucleic acids according to the invention.

Moreover, the nucleic acid molecules according to the invention may contain 3'- and/or 5'-end untranslated sequences of the coding region of genes.

An "isolated" nucleic acid molecule is separated from other nucleic acid molecules which are present in the natural source of the nucleic acid, and, if it is prepared by recombinant techniques, may be additionally free from other cellular material or culture medium, or, if it is synthesized chemically, free from chemical precursors or other chemicals.

The invention furthermore encompasses the nucleic acid molecules which are complementary to the nucleotide sequences described specifically, or a segment of the former.

The nucleotide sequences according to the invention make possible the generation of probes and primers which can be used for identifying and/or cloning homologous sequences in other cell types and organisms. Such probes or primers usually encompass a nucleotide sequence region which hybridizes under stringent conditions to at least approximately 12, preferably at least approximately 25, such as, for example, approximately 40, 50 or 75, consecutive nucleotides of a sense strand of a nucleic acid sequence according to the invention or of a corresponding antisense strand.

Further nucleic acid sequences according to the invention are derived from SEQ ID NO: 21 and differ therefrom by the addition, substitution, insertion or deletion of individual or several nucleotides, but continue to encode polypeptides with the desired profile of characteristics. They may take the form of polynucleotides which are identical with the above sequences in at least approximately 50%, 55%, 60%, 65%, 70%, 80% or 90%, preferably in at least approximately 95%, 96%, 97%, 98% or 99% of the sequence positions.

Also encompassed in accordance with the invention are those nucleic acid sequences which encompass what are known as silent mutations or which are modified in comparison with a specifically mentioned sequence in accordance with the codon usage of a specific organism of origin, or host organism, as are naturally occurring variants, such as, for example, allelic variants, thereof. Another subject are sequences which can be obtained by conservative nucleotide substitutions (i.e. the amino acid in question is replaced by an amino acid of the same charge, size, polarity and/or solubility).

Another subject of the invention are the molecules derived from the specifically disclosed nucleic acids by means of sequence polymorphisms. These genetic polymorphisms may exist between individuals within a population owing to natural variation. These natural variations usually bring about a variance of from 1 to 5% in the nucleotide sequence of a gene.

The invention furthermore also encompasses nucleic acid sequences which hybridize with abovementioned coding sequences or are complementary thereto. These polynucleotides can be found when screening genomic or cDNA libraries and, if appropriate, amplified therefrom with suitable primers by means of PCR and subsequently isolated, for example using suitable probes. Another possibility is the transformation of suitable microorganisms with polynucleotides according to the invention or vectors, the multiplication of the microorganisms, and thus amplification of the polynucleotides, and their subsequent isolation. Moreover, polynucleotides according to the invention can also be synthesized chemically.

The characteristic of being capable to "hybridize" with polynucleotides is understood as meaning the ability of a polynucleotide or oligonucleotide to bind to a virtually complementary sequence under stringent conditions, while unspecific binding between non-complementary partners does not take place under these conditions. To this end, the sequences should show 70-100%, preferably 90-100% complementarity. The characteristic of complementary sequences of being capable of binding specifically with one another is exploited for example in the Northern or Southern blot technique, or in the primer hybridization in PCR or RT-PCR. Usually oligonucleotides from a length of 30 base pairs are used. Stringent conditions are understood as meaning, for example, in the Northern blot technique, the use of a wash solution, preferably 0.1×SSC buffer with 0.1% SDS (20×SSC: 3M NaCl, 0.3M Na citrate, pH 7.0) at a temperature of 50-70° C., preferably 60-65° C., for the elution of unspecifically hybridized cDNA probes or oligonucleotides. As mentioned above, only those nucleic acids remain bound to each other which show a high degree of complementarity. The setting of stringent conditions is known to the skilled worker and described, for example, in Ausubel et al., Current Protocols in Molecular Biology, John Wiley & Sons, N.Y. (1989), 6.3.1-6.3.6.

d) Isolation of the Coding metK Genes and of Other Genes

The metK genes which encode the enzyme S-adenosylmethionine synthase (EC 2.5.1.6) can be isolated in a manner known per se.

To isolate the metK genes, or else other genes of other organisms, a gene library of this organism in *Escherichia coli* (*E. coli*) is established as the first step. Establishing gene libraries is described in detail in generally known textbooks and reference books. Examples which may be mentioned are the textbook by Winnacker: Gene and Klone, Eine Einführung in die Gentechnologie [Genes and clones, An introduction to genetic engineering] (Verlag Chemie, Weinheim, Germany, 1990), or the reference book by Sambrook et al.: Molecular Cloning, A Laboratory Manual (Cold Spring Harbor Laboratory Press, 1989). A very well known gene library is that of *E. coli* K-12 strain W3110, which has been established by Kohara et al. (Cell 50, 495-508 (198)) in λ vectors.

Cosmids, such as the cosmid vector SuperCos I (Wahl et al. (1987), Proceedings of the National Academy of Sciences USA 84: 2160-2164), but also plasmids such as pBR322 (Bolivar; Life Sciences, 25, 807-818 (1979)) or pUC9 (Vieira et al., 1982, Gene, 19: 259-268), may be used for establishing a gene library in *E. coli*. *E. coli* strains which are particularly suitable as hosts are those which are restriction deficient and recombination deficient. An example is the strain DH5αmcr, which has been described by Grant et al. (Proceedings of the National Academy of Sciences USA, 87 (1990) 4645-4649). The long DNA fragments which are cloned with the aid of cosmids can, in turn, subsequently be subcloned into customary vectors which are suitable for sequencing and subsequently sequenced, as is described for example by Sanger et al. (Proceedings of the National Academy of Sciences of the United States of America, 74: 5463-5467, 1977).

The resulting DNA sequences can then be studied with known algorithsms or sequence analysis programs, such as, for example, the program by Staden (Nucleic Acids Research (1986) 14,217-232), the program by Marck (Nucleic Acids Research (1988) 16, 1829-1836) or Butler's GCG program (Methods of Biochemical Analysis (1998) 39, 74-97).

The skilled worker will find protocols for identifying DNA sequences by means of hybridizing in, inter alia, the reference book "The DIG System Users Guide for Filter Hybridization" by Boehringer Mannheim GmbH (Mannheim, Germany, 1993) and in Liebl et al. (International Journal of Systematic Bacteriology (1991) 41: 255-260). The skilled worker will find protocols for amplifying DNA sequences with the aid of the polymerase chain reaction (PCR) in, inter alia, the reference book by Gait: Oligonucleotide synthesis: A Practical Approach (IRL Press, Oxford, UK, 1984) and in Newton and Graham: PCR (Spektrum Akademischer Verlag, Heidelberg, Germany, 1994).

It is furthermore known that modifications of the N and/or C terminus of a protein do not substantially affect the function of the latter; indeed, they are even capable of stabilizing it. The skilled worker will find information on this subject in, inter alia, Ben-Bassat et al. (1987) Journal of Bacteriology 169: 751-757, in O'Regan et al. (1989) Gene 77: 237-251, in Sahin-Toth et al. (1994) Protein Sciences 3: 240-247, in Hochuli et al. (1988) Biotechnology 6: 1321-1325 and in known textbooks of genetic and molecular biology.

e) Host Cells Used in Accordance with the Invention

Host cells which are used for the method according to the invention are, preferably, coryneform bacteria whose reduced metK activity can be detected via at least one of the following characteristics:

a) an intracellular S-adenosylmethionine titer which is reduced in comparison with the wild-type strain, b) a reduced intracellular S-adenosylmethionine synthase concentration (less S-adenosylmethionine synthase based on the total protein), or c) a reduced intracellular S-adenosylmethionine synthase activity (less S-adenosyl-methionine synthase enzyme activity based on the S-adenosylmethionine synthase protein content.

All of these characteristics can be determined by the skilled worker in a simple manner, if appropriate taking into consideration the above description.

The invention furthermore relates in particular to microorganisms which act as host cells, in particular coryneform bacteria which contain a vector, in particular shuttle vector or plasmid vector which bears at least one metK gene as defined in accordance with the invention, or coryneform bacteria in which a metK gene according to the invention with reduced activity is expressed.

These microorganisms are capable of producing sulfur-containing fine chemicals, in particular L-methionine, from glucose, sucrose, lactose, fructose, maltose, molasses, starch, cellulose or from glycerol and ethanol. They are preferably coryneform bacteria, in particular of the genus *Corynebacterium*. Among the genus *Corynebacterium*, the species *Corynebacterium glutamicum*, which is known in expert circles for its ability to produce L-amino acids, must be mentioned in particular.

Examples which must be mentioned of suitable strains of coryneform bacteria are those of the genus *Corynebacterium*, in particular of the species *Corynebacterium glutamicum* (*C. glutamicum*), such as

*Corynebacterium glutamicum* ATCC 13032,
*Corynebacterium acetoglutamicum* ATCC 15806,
*Corynebacterium acetoacidophilum* ATCC 13870,
*Corynebacterium thermoaminogenes* FERM BP-1539,
*Corynebacterium melassecola* ATCC 17965 or of the genus *Brevibacterium*, such as

*Brevibacterium flavum* ATCC 14067
*Brevibacterium lactofermentum* ATCC 13869 and
*Brevibacterium divaricatum* ATCC 14020, or strains derived from them, such as

*Corynebacterium glutamicum* KFCC10065
*Corynebacterium glutamicum* ATCC21608 which likewise produce the desired fine chemical or its precursor(s) (KFCC=Korean Federation of Culture Collection; ATCC=American Type Culture Collection)

f) Carrying Out the Fermentation According to the Invention

It has been found in accordance with the invention that coryneform bacteria, after expressing a metK gene according to the invention, produce sulfur-containing fine chemicals, in particular L-methionine, in an advantageous manner.

Various measures may be taken by the skilled worker, either individually or in combination, in order to reduce the activity or amount of an enzyme, for example S-adenosylmethionine synthase, metK. The concentration of the protein in question can be reduced by reducing the transcription frequency of the gene which encodes the protein according to the invention. This can be achieved by the skilled worker by modifying or substituting the promoter region, the regulatory region or else the ribosome binding site of the coding gene. Downstream of the coding region, the skilled worker can modify terminators or insert sequences which lead to reduced stability of the transcript. These measures, which reduce the lifespan of the mRNA, make it possible to diminish the expression of the corresponding protein and thus its concentration.

At the level of the expressed enzyme, fused sequences may lead to an increased breakdown rate and thus likewise to a reduced concentration of the protein. Moreover, the skilled worker can modify the activity, substrate affinity and substrate specificity by subjecting the coding gene to directed or undirected mutagenesis. The activity of enzymes can be influenced by mutations in the corresponding genes in such a way that the result is a degree of, or complete, reduction of the reaction rate of the enzyme reaction. Examples of such mutations are known to the skilled worker (Motoyama H. Yano H. Terasaki Y. Anazawa H. Applied & Environmental Microbiology. 67:3064-70, 2001, Eikmanns B J. Eggeling L. Sahm H. Antonie van Leeuwenhoek. 64:145-63, 1993-94). Mutants of the protein may also lead to reduced or hindered homo- or heteromultimerization of enzyme complexes and thus again to a deterioration of the enzymatic properties.

Genes which have been modified in such a way may be present either in plasmids or, preferably, integrated into the chromosome. The original gene, which has not been modified in this manner, may additionally still be present, but is preferably substituted for the modified gene.

In order to reduce the activity of an enzyme, for example S-adenosylmethionine synthase (metK), as measured in a coryneform bacterium, it may suffice to express genes which encode functional equivalents, such as artificially generated mutants or natural homologs from other organisms. The original gene may additionally be present, but is preferably substituted by the modified or homologous gene.

When producing sulfur-containing fine chemicals, in particular L-methionine, in coryneform bacteria by means of fermentation it may additionally be advantageous not only to express a metK gene according to the invention, but also to enhance one or more enzymes of the biosynthetic pathway in question, of the cysteine metabolic pathway, of the aspartate semialdehyde synthesis, of glycolysis, of anaplerotics, of the pentose-phosphate metabolism, of the citrate cycle or of the amino acid export.

Thus, one or more of the following genes may be enhanced for the production of sulfur-containing fine chemicals, in particular L-methionine:

the gene lysC, which encodes an aspartate kinase (EP 1 108 790 A2; DNA-SEQ NO. 281), the gene asd, which encodes an aspartate semialdehyde (EP 1 108 790 A2; DNA-SEQ NO. 282), the gene gap, which encodes glycerinaldehyde-3-phosphate dehydrogenase (Eikmanns (1992), Journal of Bacteriology 174: 6076-6086), the gene pgk, which encodes 3-phosphoglycerate kinase (Eikmanns (1992), Journal of Bacteriology 174: 6076-6086), the gene pyc, which encodes pyruvate carboxylase (Eikmanns (1992), Journal of Bacteriology 174: 6076-6086), the gene tpi, which encodes triose-phosphate isomerase (Eikmanns (1992), Journal of Bacteriology 174: 6076-6086), the gene metA, which encodes homoserine O-acetyltransferase (EP 1 108 790 A2; DNA-SEQ NO. 725), the gene metB, which encodes cystathionine-gamma synthase (EP 1 108 790 A2; DNA-SEQ NO. 3491), the gene metC, which encodes cystathionine-gamma lyase (EP 1 108 790 A2; DNA-SEQ NO. 3061), the gene mett, which encodes methionine-synthase (EP 1 108 790 A2; DNA-SEQ NO. 1663), the gene glyA, which encodes serine hydroxymethyltransferase (EP 1 108 790 A2; DNA-SEQ NO. 1110), the gene mety, which encodes O-acetylhomoserine sulfhydrylase (EP 1 108 790 A2; DNA-SEQ NO. 726), the gene metF, which encodes methylenetetrahydrofolate reducase (EP 1 108 790 A2; DNA-SEQ NO. 2379), the gene serC, which encodes phosphoserine aminotransferase (EP 1 108 790 A2; DNA-SEQ NO. 928)

a gene serB encoding phosphoserine-phosphatase (EP 1 108 790 A2; DNA-SEQ NO. 334, DNA-SEQ NO. 467, DNA-SEQ NO. 2767)

the gene cysE, which encodes serine acetyl transferase (EP 1 108 790 A2; DNA-SEQ NO. 2818)

the gene cysK, which encodes cysteine synthase (EP 1 108 790 A2; DNA-SEQ NO. 2817), the gene hom, which encodes a homoserine dehydrogenase (EP 1 108 790 A2; DNA-SEQ NO. 1306)

Thus, it may be advantageous for the production of sulfur-containing fine chemicals, in particular L-methionine in coryneform bacteria simultaneously to mutate at least one of the following genes such that the corresponding proteins are affected less or not at all by a metabolite with regard to their activity with comparison with unmutated proteins, or so that their specific activity is enhanced:

the gene lysC, which encodes an aspartate kinase (EP 1 108 790 A2; DNA-SEQ NO. 281), the gene pyc, which encodes pyruvate carboxylase (Eikmanns (1992), Journal of Bacteriology 174: 6076-6086), the gene metA, which encodes homoserine O-acetyltransferase (EP 1 108 790 A2; DNA-SEQ NO. 725), the gene metB, which encodes cystathionine-gamma synthase (EP 1 108 790 A2; DNA-SEQ NO. 3491), the gene metC, which encodes cystathionine-gamma lyase (EP 1 108 790 A2; DNA-SEQ NO. 3061), the gene metH, which encodes methionine synthase (EP 1 108 790 A2; DNA-SEQ NO. 1663), the gene glyA, which encodes serine hydroxymethyltransferase (EP 1 108 790 A2; DNA-SEQ NO. 1110), the gene metY, which encodes O-acetylhomoserine sulfhydrylase (EP 1 108 790 A2; DNA-SEQ NO. 726), the gene metF, which encodes methylene tetrahydrofolate reductase (EP 1 108 790 A2; DNA-SEQ NO. 2379), the gene serC, which encodes phosphoserine aminotransferase (EP 1 108 790 A2; DNA-SEQ NO. 928)

a gene serB which encodes phosphoserine-phosphatase (EP 1 108 790 A2; DNA-SEQ NO. 334, DNA-SEQ NO. 467, DNA-SEQ NO. 2767)

the gene cysE, which encodes serine acetyltransferase (EP 1 108 790 A2; DNA-SEQ NO. 2818)

the gene cysK, which encodes cysteine synthase (EP 1 108 790 A2; DNA-SEQ NO. 2817), the gene hom, which encodes homoserine dehydrogenase (EP 1 108 790 A2; DNA-SEQ NO. 1306)

Moreover, it may be advantageous for the production of sulfur-containing fine chemicals, in particular L-methionine, additionally to the expression of one of the metK genes according to the invention to attenuate one or more of the following genes, in particular to reduce or switch off their expression:

the gene thrB, which encodes homoserine kinase (EP 1 108 790 A2; DNA-SEQ NO. 3453)

the gene ilvA, which encodes threonine dehydratase (EP 1 108 790 A2; DNA-SEQ NO. 2328)

the gene thrC, which encodes threonine synthase (EP 1 108 790 A2; DNA-SEQ NO. 3486)

the gene ddh, which encodes meso-diaminopimelate D-dehydrogenase (EP 1 108 790 A2; DNA-SEQ NO. 3494)

the gene pck, which encodes phosphoenolpyruvate carboxykinase (EP 1 108 790 A2; DNA-SEQ NO. 3157)

the gene pgi, which encodes glucose-6-phosphate 6-isomerase (EP 1 108 790 A2; DNA-SEQ NO. 950)

the gene poxB, which encodes pyruvate oxidase (EP 1 108 790 A2; DNA-SEQ NO. 2873)

the gene dapA, which encodes dihydrodipicolinate synthase (EP 1 108 790 A2; DNA-SEQ NO. 3476)

the gene dapB, which encodes dihydrodipicolinate reductase (EP 1 108 790 A2; DNA-SEQ NO. 3477)

the gene lysA, which encodes diaminopicolinate decarboxylase (EP 1 108 790 A2; DNA-SEQ NO. 3451)

Furthermore, it may be advantageous for the production of sulfur-containing fine chemicals, in particular L-methionine, additionally to the expressionof one of the metK genes according to the invention in coryneform bacteria simultaneously to mutate at least one the following genes in such a way that the enzyme activity of the corresponding protein is reduced to a degree or completely:

the gene thrB, which encodes homoserine kinase (EP 1 108 790 A2; DNA-SEQ NO. 3453)

the gene ilvA, which encodes threonine dehydratase (EP 1 108 790 A2; DNA-SEQ NO. 2328)

the gene thrC, which encodes threonine synthase (EP 1 108 790 A2; DNA-SEQ NO. 3486)

the gene ddh, which encodes meso-diaminopimelate D-dehydrogenase (EP 1 108 790 A2; DNA-SEQ NO. 3494)

the gene pck, which encodes phosphoenolpyruvate carboxykinase (EP 1 108 790 A2; DNA-SEQ NO. 3157)

the gene pgi, which encodes glucose-6-phosphate 6-isomerase (EP 1 108 790 A2; DNA-SEQ NO. 950)

the gene poxB, which encodes pyruvate oxidase (EP 1 108 790 A2; DNA-SEQ NO. 2873)

the gene dapA, which encodes dihydrodipicolinate synthase (EP 1 108 790 A2; DNA-SEQ NO. 3476)

the gene dapB, which encodes dihydrodipicolinate reductase (EP 1 108 790 A2; DNA-SEQ NO. 3477)

the gene lysA, which encodes diaminopicolinate decarboxylase (EP 1 108 790 A2; DNA-SEQ NO. 3451)

Furthermore, it may be advantageous for the production of sulfur-containing fine chemicals, in particular L-methionine, in addition to the expression of a metK gene according to the invention to eliminate undesired secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The skilled worker can take various measures, individually or in combination, in order to achieve overexpression. Thus, the copy number of the genes in question can be increased, or the promoter region and regulatory region or the ribosome binding site which is located upstream of the structural gene can be mutated. Expression cassettes which are introduced upstream of the structural gene act in the same fashion. In addition, inducible promoters make it possible to increase expression during the production of L-methionine by fermentation. Expression is also improved by measures which extend the life of mRNA.

Moreover, the enzyme activity is also increased by preventing the degradation of the enzyme protein. The genes or gene constructs can either be present in plasmids with different copy numbers or else be integrated and amplified in the chromosome. As an alternative, overexpression of the genes in question can furthermore be achieved by modifying the media composition and fermentation process.

The skilled worker will find information on the subject in, inter alia, Martin et al. (Biotechnology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP 0472869, in U.S. Pat. No. 4,601,893, in Schwarzer and Pühler (Biotechnology 9, 84-87 (1991), in Remscheid et al. (Applied and Environmental Microbiology 60,126-132 (1994), in LaBarre et al. (Journal of Bacteriology 175, 1001-1007 (1993)), in WO 96/15246, in Malumbres et al. (Gene 134, 15-24 (1993)), in JP-A-10-229891, in Jensen and Hammer (Biotechnology and Bioengineering 58, 191-195 (1998)), in Makrides (Microbiological Reviews 60:512-538 (1996) and in known textbooks of genetics and molecular biology.

The invention therefore also relates to expression constructs comprising a nucleic acid sequence encoding a polypeptide according to the invention under the genetic control of regulatory nucleic acid sequences, and to vectors encompassing at least one of these expression constructs. Preferably, such constructs according to the invention comprise a promoter 5'-upstream of the coding sequence in question and, 3'-downstream, a termination sequence and, if appropriate, further customary regulatory elements, in each case in operative linkage with the coding sequence. "Operative linkage" is understood as meaning the sequential arrangement of promoter, coding sequence, terminator and, if appropriate, further regulatory elements in such a way that each of the regulatory elements can fulfill its intended function upon expression of the coding sequence. Examples of sequences capable of operative linkage are activation sequences and enhancers and the like. Further regulatory elements encompass selectable markers, amplification signals, replication origins and the like. Suitable regulatory sequences are described, for example, in Goeddel, Gene Expression Technology: Methods in Enzymology 185, Academic Press, San Diego, Calif. (1990).

The natural regulatory sequence may still be present upstream of the actual structural gene, in addition to the artificial regulatory sequences. If appropriate, this natural regulation can be eliminated by genetic modification, and gene expression can be increased or reduced. However, the gene construct may also be simpler in construction, that is to say no additional regulatory signals are inserted before the structural gene, and the natural promoter with its regulation is not removed. Instead, the natural regulatory sequence is mutated in such a way that regulation no longer takes place, and gene expression is increased or reduced. One or more copies of the nucleic acid sequences may be present in the gene construct.

Examples of useful promoters are: the promoters ddh, amy, lysC, dapA, lysA from *Corynebacterium glutamicum*, but also Gram-positive promoters SPO2 as are described in Bacillus Subtilis and Its Closest Relatives, Sonenshein, Abraham L., Hoch, James A., Losick, Richard; ASM Press, District of Columbia, Wash. and Patek M. Eikmanns B J. Patek J. Sahm H. Microbiology. 142 1297-309, 1996, or else cos, tac, trp, tet, trp-tet, lpp, lac, lpp-lac, lacIq, T7, T5, T3, gal, trc, ara, SP6, l-PR or l-PL promoters, which are advantageously used in Gram-negative bacteria. Also preferred is the use of inducible promoters, such as, for example, light-inducible and, in particular, temperature-inducible promoters, such as the $P_rP_l$ promoter. In principle, all natural promoters together with their regulatory sequences may be used. In addition, synthetic promoters may also be used advantageously.

The abovementioned regulatory sequences are intended to make possible the targeted expression of the nucleic acid sequences and of protein expression. Depending on the host organism, this may mean, for example, that the gene is expressed or overexpressed only after induction, or that it is expressed and/or overexpressed immediately.

In this context, the regulatory sequences or factors can preferably have an adverse effect on expression, thus reducing it. Thus, diminution may take place at the transcriptional level by using weak transcription signals such as promoters and/or enhancers. However, diminution of translation is also possible, for example by reducing mRNA stability.

In this context, the regulatory sequences or factors may preferably have a positive effect on expression, thus increasing or reducing it. Thus, an enhancement of the regulatory elements may advantageously take place at the transcriptional level by using strong transcription signals such as promoters and/or enhancers. However, enhancement of translation is also possible, for example by increasing mRNA stability.

An expression cassette is generated by fusing a suitable promoter, a suitable Shine-Dalgarno sequence with a metK nucleotide sequence and a suitable termination signal. Customary recombination and cloning techniques as are described, for example, in Current Protocols in Molecular Biology, 1993, John Wiley & Sons, Incorporated, New York N.Y., PCR Methods, Gelfand, David H., Innis, Michael A., Sinsky, John J. 1999, Academic Press, Incorporated, Calif., San Diego, PCR Cloning Protocols, Methods in Molecular Biology Ser., Vol. 192, 2nd ed., Humana Press, New Jersey, Totowa. T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987) are used for this purpose.

For expression in a suitable host organism, the recombinant nucleic acid construct or gene construct is advantageously inserted into a host-specific vector which makes possible optimal expression of the genes in the host. Vectors are well known to the skilled worker and can be found, for example, in "Cloning Vectors" (Pouwels P. H. et al., Ed., Elsevier, Amsterdam-New York-Oxford, 1985). Apart from plasmids, vectors are also understood as meaning all the other vectors with which the skilled worker is familiar, such as, for example, phages, transposons, IS elements, phagemids, cosmids, and linear or circular DNA. These vectors can be replicated autonomously in the host organism or else replicated chromosomally.

metK genes according to the invention are expressed for example with the aid of episomal plasmids. Suitable plasmids are those which are replicated in coryneform bacteria. A large number of know plasmid vectors, such as, for example, pZ1 (Menkel et al., Applied and Environmental Microbiology (1989) 64: 549-554), pEKEx1 (Eikmanns et al., Gene 102: 93-98 (1991)) or pHS2-1 (Sonnen et al., Gene 107: 69-74 (1991)), are based on the cryptic plasmids pHM1519, pBL1 or pGA1. Other plasmid vectors, such as, for example, pCLiK5MCS, SEQ ID NO: 9, or those which are based on pCG4 (U.S. Pat. No. 4,489,160) or pNG2 (Serwold-Davis et al., FEMS Microbiology Letters 66, 119-124 (1990)) or pAG1 (U.S. Pat. No. 5,158,891) may likewise be used.

Other suitable plasmid vectors are those with the aid of which the method of gene amplification by integration into the chromosome can be applied, as has been described, for example, by Remscheid et al. (Applied and Environmental Microbiology 60,126-132 (1994)) for duplicating or amplifying the hom-thrB operon. In this method, the complete gene is cloned into a plasmid vector which is capable of replication in a host (typically E. coli), but not in C. glutamicum. Suitable vectors are, for example, pSUP301 (Simon et al., Bio/Technology 1,784-791 (1983)), pK18mob or pK19mob (Schafer et al., Gene 145,69-73 (1994)), Bernard et al., Journal of Molecular Biology, 234: 534-541 (1993)), pEM1 (Schrumpf et al. 1991, Journal of Bacteriology 173: 4510-4516) or pBGS8 (Spratt et al., 1986, Gene 41: 337-342). Other plasmid vectors, such as, for example, pCLiK5MCS integrative sacB, SEQ ID NO:12, may likewise be used.

The plasmid vector containing the gene to be amplified is subsequently transferred into the desired C. glutamicum strain by transformation. Transformation methods are described, for example, by Thierbach et al. (Applied Microbiology and Biotechnology 29, 356-362 (1988)), Dunican and Shivnan (Biotechnology 7, 1067-1070 (1989)) and Tauch et al. (FEMS Microbiological Letters 123,343-347 (1994)).

The microorganisms which have been produced in accordance with the invention can be grown continuously or discontinuously by the batch method, the fed-batch method or the repeated fed-batch method for producing sulfur-containing fine chemicals, in particular L-methionine. An overview over known culture methods can be found in the textbook by Chmiel (Bioprozeβtechnik 1. Einführung in die Bioverfahrenstechnik [Bioprocess Engineering 1. Introduction to Bioprocess Technology] (Gustav Fischer Verlag, Stuttgart, 1991)) or in the textbook by Storhas (Bioreaktoren and periphere Einrichtungen [Bioreactors and Peripheral Units] (Vieweg Verlag, Brunswick/Wiesbaden, 1994)).

The culture medium to be used must suitably meet the needs of the strains in question. Descriptions of culture media for a variety of microorganisms are found in the manual "Manual of Methods fur General Bacteriology" of the American Society for Bacteriology (Washington D.C., USA, 1981).

These media which can be employed in accordance with the invention usually encompass one or more carbon sources, nitrogen sources, inorganic salts, vitamins and/or trace elements.

Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch or cellulose. Sugars may also be added to the media via complex compounds, such as molasses, or other by-products of sugar refining. It may also be advantageous to add mixtures of various carbon sources. Other possible carbon sources are oils and fats such as, for example, soya oil, sunflower oil, peanut oil and coconut fat, fatty acids such as, for example, palmitic acid, stearic acid or linoleic acid, alcohols such as, for example, glycerol, methanol or ethanol, and organic acids such as, for example, acetic acid or lactic acid.

Nitrogen sources are usually organic or inorganic nitrogen compounds or materials comprising these compounds. Examples of nitrogen sources encompass ammonia gas or ammonium salts such as ammonium sulfate, ammonium chloride, ammonium phosphate, ammonium carbonate or ammonium nitrate, nitrates, urea, amino acids or complex nitrogen sources such as corn steep liquor, soya meal, soya protein, yeast extract, meat extract and others. The nitrogen sources can be used individually or as a mixture.

Inorganic salt compounds which may be present in the media encompass the chloride, phosphorus or sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, but also organic sulfur compounds, such as mercaptans and thiols, may be used as sulfur source for the production of sulfur-containing fine chemicals, in particular of methionine.

Phosphoric acid, potassium dihydrogenphosphate or dipotassium hydrogenphosphate or the corresponding sodium-containing salts may be used as phosphorus source.

Sequestrants may be added to the medium in order to maintain the metal ions in solution. Particularly suitable sequestrants encompass dihydroxyphenols, such as catechol or protocatechuate, or organic acids such as citric acid.

Usually, the fermantation media employed in accordance with the invention also comprise other growth factors such as vitamins or growth promoters, which include, for example, biotin, riboflavin, thiamine, folic acid, nicotinic acid, panthothenate and pyridoxine. Growth factors and salts are frequently obtained from complex media components such as yeast extract, molasses, corn steep liquor and the like. Moreover, suitable precursors may be added to the culture medium. The exact composition of the compounds in the media depends greatly on the experiment in question and will be decided individually for each individual case. Information on the optimization of media can be found in the textbook "Applied Microbiol. Physiology, A Practical Approach" (Ed. P. M. Rhodes, P. F. Stanbury, IRL Press (1997) pp. 53-73, ISBN 0 19 963577 3). Growth media can also be obtained from commercial sources, such as Standard 1 (Merck) or BHI (brain heart infusion, DIFCO) and the like.

All components of media are sterilized, either by means of heat (20 minutes at 1.5 bar and 121° C.) or by filter sterilization. The components may be sterilized either together or, if appropriate, separately. All of the components of the media may be present at the beginning of the fermentation or else be added continuously or batchwise, as desired.

The culture temperature is normally between 15° C. and 45° C., preferably 25° C. to 40° C., and can be kept constant during the experiment or else be varied. The pH of the medium should be in the range of from 5 to 8.5, preferably around 7.0. The pH for the fermentation can be controlled during the fermentation by addition of basic compounds such as sodium hydroxide, potassium hydroxide, ammonia or ammonia water, or acidic compounds such as phosphoric acid or sulfuric acid. Antifoam agents such as, for example, fatty acid polyglycol esters may be employed to control foam development. To maintain plasmid stability, suitable selectively acting substances such as, for example, antibiotics may be added to the medium. To maintain aerobic conditions, oxygen or oxygen-containing gas mixtures, for example ambient air, are passed into the culture. The culture temperature is normally 20° C. to 45° C., preferably 25° C. to 40° C. Fermentation is continued until a maximum of the desired product has formed. This aim is normally achieved within 10 hours to 160 hours.

The fermentation broths obtained in this way, in particular fermentation broths comprising L-methionine, usually contain a dry biomass of 7.5 to 25% by weight.

An additional advantage is to carry out the fermentation under sugar limitation conditions, at least at the end, but in particular over at least 30% of the fermentation period. This means that during this time the concentration of utilizable sugar in the fermentation medium is maintained at or reduced to >0 to 3 g/l.

The fermentation broth is then processed further. According to requirement, all or some of the biomass may be removed from the fermentation broth by separation methods such as, for example, centrifugation, filtration, decanting or a combination of these methods, or else be left completely in said broth.

Subsequently, the fermentation broth may be thickened or concentrated with the aid of known methods, such as, for example, with the aid of a rotary evaporator, a thin-film evaporator, a falling-film evaporator, by reverse osmosis, or by nanofiltration. This concentrated fermentation broth can then be worked up by freeze drying, spray drying, spray granulation or by other methods.

However, it is also possible to further purify the sulfur-containing fine chemicals, in particular L-methionine. To this end, the product-containing broth, after removing the biomass, is subjected to a chromatography using a suitable resin, with all or some of the desired product or contaminants being retained on the chromatography resin. These chromatography steps can be repeated, if necessary, using the same or other chromatography resins. The skilled worker is familiar with the selection of suitable chromatography resins and their most effective use. The purified product can be concentrated by filtration or ultrafiltration and stored at a temperature at which the stability of the product is greatest.

The identity and purity of the isolated compound(s) can be determined by techniques of the art. These include high performance liquid chromatography (HPLC), spectroscopic methods, staining methods, thin-layer chromatography, NIRS, enzyme assay or microbiological assays. These analytic methods are summarized in: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ulmann's Encyclopedia of Industrial Chemistry (1996) vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Volume 17.

The following nonlimiting examples describe the invention in more detail:

FIG. 1 shows the results of a radioactive metK assay using wild-type enzyme and C94A mutants, respectively.

EXAMPLE 1

Construction of the Vector pCLiK5MCS

First ampicillin resistance and origin of replication of the vector pBR322 were amplified using the oligonucleotide primers SEQ ID NO: 1 and SEQ ID NO: 2 with the aid of the polymerase chain reaction (PCR).

SEQ ID NO:1
5'-CCCGGGATCCGCTAGCGGCGCGCCGGCCGGCCCGGTGTGAAATACCG CACAG-3'

SEQ ID NO:2
5'-TCTAGACTCGAGCGGCCGCGGCCGGCCTTTAAATTGAAGACGAAAGG GCCTCG-3'

In addition to the sequences complementary to pBR322, the oligonucleotide primer SEQ ID NO: 1 contains in 5'-3' direction the cleavage sites for the restriction nucleases SmaI, BamHI, NheI and AscI and the oligonucleotide primer SEQ ID NO: 2 contains in 5'-3' direction the cleavage sites for the restriction endonucleases XbaI, XhoI, NotI and DraI. The PCR reaction was carried out according to a standard method such as that by Innis et al. (PCR Protocols. A Guide to Methods and Applications, Academic Press (1990)) using Pfu-Turbo polymerase (Stratagene, La Jolla, USA). The DNA fragment obtained of approximately 2.1 kb in size was purified using the GFX™PCR, DNA and gel band purification kit (Amersham Pharmacia, Freiburg) according to the manufacturer's instructions. The blunt ends of the DNA fragment were ligated to one another using the rapid DNA ligation kit (Roche Diagnostics, Mannheim) according to the manufacturer's instructions and the ligation mixture was transformed into competent E. coli XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected by plating out onto ampicillin (50 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK1.

Starting from plasmid pWLT1 (Liebl et al., 1992) as template for a PCR reaction, a kanamycin resistance cassette was amplified using the oligonucleotide primers SEQ ID NO: 3 and SEQ ID NO: 4.

```
SEQ ID NO:3:
5'-GAGATCTAGACCCGGGGATCCGCTAGCGGGCTGCTAAAGGAAGCGG
A-3'

SEQ ID NO:4:
5'-GAGAGGCGCGCCGCTAGCGTGGGCGAAGAACTCCAGCA-3'
```

Apart from the sequences complementary to pWLT1, the oligonucleotide primer SEQ ID NO:3 contains in 5'-3' direction the cleavage sites for the restriction endonucleases XbaI, SmaI, BamHI, NheI and the oligonucleotide primer SEQ ID NO: 4 contains in the 5'-3' direction the cleavage sites for the restriction endonucleases AscI and NheI. The PCR reaction was carried out using PfuTurbo polymerase (Stratagene, La Jolla, USA) according to a standard method such as that of Innis et al. (PCR Protocols. A Guide to Methods and Applications, Academic Press (1990)). The DNA fragment obtained approximately 1.3 kb in size was purified using the GFX™PCR, DNA and gel band purification kit (Amersham Pharmacia, Freiburg) according to the manufacturer's instructions. The DNA fragment was cleaved with restriction endonucleases XbaI and AscI (New England Biolabs, Beverly, USA) and, following that, again purified using the GFX™MPCR, DNA and gel band purification kit (Amersham Pharmacia, Freiburg) according to the manufacturer's instructions. The vector pCLiK1 was likewise cleaved with the restriction endonucleases XbaI and AscI and dephosphorylated using alkaline phosphatase I (Roche Diagnostics, Mannheim) according to the manufacturer's instructions. After electrophoresis in a 0.8% strength agarose gel, the linearized vector (approx. 2.1 kb) was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent E. coli XL-1Blue (Stratagene, La Jolla, USA) according to standard methods, as described in Sambrook et al. (Molecular Cloning. A Laboratory Manual, Cold Spring Harbor, (1989)). Plasmid-carrying cells were selected by plating out onto ampicillin (50 µg/ml) and kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK2.

The vector pCLiK2 was cleaved with the restriction endonuclease DraI (New England Biolabs, Beverly, USA). After electrophoresis in 0.8% strength agarose gel, an approx. 2.3 kb vector fragment was isolated using the GFX™PCR, DNA and gel band purification kit (Amersham Pharmacia, Freiburg) according to the manufacturer's instructions. This vector fragment was religated with the aid of the rapid DNA ligation kit (Roche Diagnostics, Mannheim) according to the manufacturer's instructions and the ligation mixture was transformed into competent E. coli XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK3.

Starting from plasmid pWLQ2 (Liebl et al., 1992) as template for a PCR reaction, the origin of replication pHM1519 was amplified using the oligonucleotide primers SEQ ID NO: 5 and SEQ ID NO:6.

```
SEQ ID NO:5:
5'-GAGAGGGCGGCCGCGCAAAGTCCCGCTTCGTGAA-3'

SEQ ID NO:6:
5'-GAGAGGGCGGCCGCTCAAGTCGGTCAAGCCACGC-3'
```

Apart from the sequences complementary to pWLQ2, the oligonucleotide primers SEQ ID NO:5 and SEQ ID NO:6 contain cleavage sites for the restriction endonuclease NotI. The PCR reaction was carried out using PfuTurbo polymerase (Stratagene, La Jolla, USA) according to a standard method such as that of Innis et al. (PCR Protocols. A Guide to Methods and Applications, Academic Press (1990)). The DNA fragment obtained approximately 2.7 kb in size was purified using the GFX™PCR, DNA and gel band purification kit (Amersham Pharmacia, Freiburg) according to the manufacturer's instructions. The DNA fragment was cleaved with restriction endonuclease NotI (New England Biolabs, Beverly, USA) and, following that, again purified using the GFX™PCR, DNA and gel band purification kit (Amersham Pharmacia, Freiburg) according to the manufacturer's instructions. The vector pCLiK3 was likewise cleaved with the restriction endonuclease NotI and dephosphorylated using alkaline phosphatase I (Roche Diagnostics, Mannheim) according to the manufacturer's instructions. After electrophoresis in a 0.8% strength agarose gel, the linearized vector (approx. 2.3 kb) was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent E. coli XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK5.

pCLiK5 was extended by a multiple cloning site (MCS) by combining the two synthetic essentially complementary oligonucleotides SEQ ID NO:7 and SEQ ID NO:8, which contain cleavage sites for the restriction endonucleases SwaI, XhoI, AatI, ApaI, Asp718, MluI, NdeI, SpeI, EcoRV, SalI, ClaI, BamHI, XbaI and SmaI to give a double-stranded DNA fragment by heating them together to 95° C. followed by slow cooling.

```
SEQ ID NO:7:
5'-TCGAATTTAAATCTCGAGAGGCCTGACGTCGGGCCCGGTACCACGCG

TCATATGACTAGTTCGGACCTAGGGATATCGTCGACATCGATGCTCTTCT

GCGTTAATTAACAATTGGGATCCTCTAGACCCGGGATTTAAAT-3'

SEQ ID NO:8:
5'-GATCATTTAAATCCCGGGTCTAGAGGATCCCAATTGTTAATTAACGC

AGAAGAGCATCGATGTCGACGATATCCCTAGGTCCGAACTAGTCATATGA

CGCGTGGTACCGGGCCCGACGTCAGGCCTCTCGAGATTTAAAT-3'
```

The vector pCLiK5 was cleaved with the restriction endonucleases XhoI and BamHI (New England Biolabs, Beverly, USA) and dephosphorylatted using alkaline phosphatase I (Roche Diagnostics, Mannheim) according to the manufacturer's instructions. After electrophoresis in a 0.8% strength agarose gel, the linearized vector (approx. 5.0 kb) was isolated using the GFX™PCR, DNA and gel band purification kit (Amersham Pharmacia, Freiburg) according to the manufacturer's instructions. This vector fragment was ligated with the synthetic double-stranded DNA fragment with the aid of the rapid DNA ligation kit (Roche Diagnostics, Mannheim) according to the manufacturer's instructions and the ligation mixture was transformed into competent E. coli XL-1 Blue (Stratagene, La Jolla, USA) according to standard methods as described in Sambrook et al. (Molecular Cloning. A Laboratory Manual, Cold Spring Harbor, (1989)). Plasmid-carrying cells were selected by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK5MCS.

Sequencing reactions were carried out according to Sanger et al. (1977) Proceedings of the National Academy of Sciences USA 74:5463-5467. The sequencing reactions were fractionated and analyzed by means of ABI Prism 377 (PE Applied Biosystems, Weiterstadt).

The resultant plasmid pCLiK5MCS is listed as SEQ ID NO:9.

EXAMPLE 2

Construction of the vector pCLiK5MCS integrativ sacB

Starting from the plasmid pK19mob (Schafer et al., Gene 145,69-73(1994)) as template for a PCR reaction, the Bacillus subtilis sacB gene was amplified using the oligonucleotide primers SEQ ID NO:10 and SEQ ID NO:11.

```
SEQ ID NO:10:
5'-GAGAGCGGCCGCCGATCCTTTTTAACCCATCAC-3'

SEQ ID NO:11:
5'-AGGAGCGGCCGCCATCGGCATTTTCTTTTGCG-3'
```

Apart from the sequences complementary to pK19mobsac, the oligonucleotide primers SEQ ID NO:10 and SEQ ID NO:11 contain cleavage sites for the restriction endonuclease NotI. The PCR reaction was carried out using PfuTurbo polymerase (Stratagene, La Jolla, USA) according to a standard method such as that of Innis et al. (PCR Protocols. A Guide to Methods and Applications, Academic Press (1990)). The DNA fragment obtained of approximately 1.9 kb in size was purified using the GFX™PCR, DNA and gel band purification kit (Amersham Pharmacia, Freiburg) according to the manufacturer's instructions. The DNA fragment was cleaved with the restriction endonuclease NotI (New England Biolabs, Beverly, USA) and, following that, again purified using the GFX™PCR, DNA and gel band purification kit (Amersham Pharmacia, Freiburg) according to the manufacturer's instructions. The vector pCLiK5MCS was likewise cleaved with the restriction endonuclease NotI and dephosphorylated using alkali phosphatase I (Roche Diagnostics, Mannheim) according to the manufacturer's instructions. After electrophoresis in a 0.8% strength agarose gel, an approximately 2.4 kb in size vector fragment was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent E. coli XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is noted pCLiK5MCS integrativ sacB.

Sequencing reactions were carried out according to Sanger et al. (1977) Proceedings of the National Academy of Sciences USA 74:5463-5467. The sequencing reactions were fractionated and analyzed by means of ABI Prism 377 (PE Applied Biosystems, Weiterstadt).

The resultant plasmid pCLiK5MCS integrativ sacB is listed as SEQ ID NO:12.

EXAMPLE 3

Isolation and cloning of the metK gene from C. glutamicum

Chromosomal C. glutamicum ATCC 13032 DNA was prepared using the method of Tauch et al. (1995) Plasmid 33:168-179 or Eikmanns et al. (1994) Microbiology 140: 1817-1828. The following oligonucleotide primers were synthesized starting from the metK sequence of Großmann et al. (2000) FEMS Microbiology Letters 193:99-103:

```
                                       SEQ ID NO:13
5'-GAGAGCCCGGGAAGAAGGGCTGCGACCTCCTCAT-3'
and

SEQ ID NO:14
5'-CTCTCACGCGTCATATGCAGGTGAGGTAACCCCA-3'
```

A 1640 base pair DNA fragment was amplified from the genomic C. glutamicum DNA using standard methods as described by Innis et al. (1990) PCR Protocols. A Guide to Methods and Applications, Academic Press using the above-mentioned oligonucleotide primers and Pfu Turbo Polymerase (Stratagene).

The fragment was cleaved with the restirction enzymes Mlu I and Sma I (Roche Diagnostics, Mannheim) which had been introduced via the PCR oligonucleotide primers and separated by gel electrophoresis. The DNA fragment was subsequently isolated from the agarose using GFX™PCR, DNA and Gel Band Purification Kit (Amersham Pharmacia, Freiburg).

The vector pCLiK5MCS, SEQ ID NO:9 was likewise cleaved with the restriction enzymes Sma I and Mlu I and dephosphorylated with alkaline phosphatase I (Roche Diagnostics, Mannheim) following the manufacturer's instructions. The vector and the DNA fragment were ligated with T4 DNA ligase (Amersham Pharmacia, Freiburg) and transformed into E. coli XL-1Blue (Stratagene) using standard methods as described by Sambrook et al. (1989), Molecular Cloning. A Laboratory Manual, Cold Spring Harbor.

Plasmid DNA was prepared by methods and materials from Quiagen. Sequencing reactions were carried out as described by Sanger et al. (1977) Proceedings of the National Academy of Sciences USA 74:5463-5467. The sequencing reactions were separated and evaluated by means of ABI Prism 377 (PE Applied Biosystems, Weiterstadt).

The resultant plasmid pCLiK5MCS/metKwt is listed as SEQ ID NO:15.

EXAMPLE 4

Mutagenesis of the C. glutamicum metK Gene

Directed mutagenesis of the C. glutamicum metK gene was carried out using the QuickChange Kit (Stratagene), following the manufacturer's instructions. The mutagenesis was carried out in plasmid pCLiK5MCS/metKwt, SEQ ID NO:15. The following oligonucleotide primers were synthesized for substituting cysteine 94 of SEQ ID NO: 16 for alanine 94:

```
                                       SEQ ID NO:17
5'-GATTCGACGGACGCACCGCTGGCGTCTCAGTATCCATC-3'
and

SEQ ID NO:18
5'-GATGGATACTGAGACGCCAGCGGTGCGTCCGTCGAATC-3'
```

The use of these oligonucleotide primers resulted in SEQ ID NO:15 in a substitution of the nucleotides in position 1056 (C was substituted by G) and 1057 (A was substituted by C). The resulting amino acid substitution Cys94Ala in the metK gene was confirmed by sequencing reactions following transformation and plasmid preparation. The plasmid was denoted pCLiK5MCS/metKC94A and is listed as SEQ ID NO:19.

SAM Synthetase (metK) Assay

C. glutamicum strains which had been transformed either with the plasmid pCLiK5MCS/metKwt, SEQ ID NO: 15 or with the plasmid pCLiK5MCS/metKC94A, SEQ ID NO: 19 were grown in BHI/glucose medium (37 g/l prepared brain heart infusion medium, Difco, 10 mM $(NH_4)_2SO_4$, 4% glucose) at 30° C. to an $OD_{600}$ of 20. The cells were spun down at 4° C. and the pellet was washed with cold physiological saline. After recentrifugation, 0.25 g of moist cell pellet was resuspended in 1 ml of disruption buffer (50 mM Tris pH 7.5, 10 mM $MgCl_2$, 50 mM KCl, 1 mM DTT) at 4° C. The bacterial suspension was lysed three times for in each case 30 seconds in a Ribolyser from Hybaid and in blue Ribolyser tubes from Hybaid and at rotation setting 6.0. The lysate was clarified by centrifugation for 45 minutes in an Eppendorf centrifuge at 13 000 rpm, and the supernatant was diluted with water 1:10. The protein content was determined by the method of Bradford, M. M. (1976) Anal. Biochem. 72:248-254.

The enzyme activity of SAM synthase was determined by the method of Markham, G. D. et al. (1983) Methods in Enzymology 94: 219-222, with the following modifications:

Reaction mixtures of 100 µl, containing 100 mM Tris pH 8.0, 100 mM KCl, 20 mM $MgCl_2$, 1.2 mM L-methionine, 10 mM ATP, 1 µl $^{35}$S-L-methionine, corresponding to 15.15 µCi (Amersham SJ204, specific activity 1 Ci/µmol) and $H_2O$ to 100 µl were started with 100 µg of the protein lysates in question and incubated at 37° C. After 0, 5, 10, 20, 30 and 60 minutes, 10 µl aliquots of the reaction mixture were removed and stopped on ice using 20 µl of 50 mM EDTA.

30 µl of the stopped reaction were placed on phosphocellulose filter units (Pierce, No. 29520) and spun down for 1 minute in an Eppendorf centrifuge at 6000 rpm. The filter was washed twice with 500 µl of 75 mM phosphoric acid and then placed into a counting tube containing scintillation liquid. The radioactivity of the S-adenosylmethionine formed is determined in a scintillation counter (Beckman).

The data are shown in the appended FIG. 1.

Taking into consideration the specific activity of the radioactive L-methionine, and the protein quantity employed, the rate of S-adenosylmethionine formation can be determined from the increase in radioactivity incorporated per unit time. Its unit is µmol S-adenosylmethionine/min*mg protein. This rate can be compared between wild-type enzyme and mutant enzyme.

EXAMPLE 6

Determination of the Cellular S-adenosylmethionine titer in C. glutamicum

To determine the cellular S-adenosylmethionine titers in C. glutamicum strains which have been transformed either with pCLiK5MCS/metKwt (SEQ ID NO:15) or pCLiK5MCS/metKC94A (SEQ ID NO:19), the following procedure was used. A cell pellet obtained as described in Example 5 which had been washed with ice-cold physiological saline was resuspended in trichloroacetic acid (200 μl of TCA per 0.1 g moist pellet). After 5 minutes on ice, the suspension was clarified for 5 minutes in an Eppendorf centrifuge at 4° C. and 13 000 rpm. The S-adenosylmethionine content in the supernatant was determined by means of HPLC (Ionospher 5C cation exchange column, injection volume 10 μl, mobile phase: 70% vol/vol 0.2 M Ammonium formate pH 4.0 30% vol/vol methanol; UV detection 260 nm; 40° C.; retention time 8.5 minutes).

TABLE 1

S-Adenosylmethionine titers

|  | mg/l |
|---|---|
| ATCC 13032 + metK | 73.94 |
| ATCC 13032 + metK C94A | 47.36 |

EXAMPLE 7

Substitution of the metK wt Gene in *C. glutamicum* for metK C94A

For the allelic substitution of the metK wild-type gene in *C. glutamicum* KFCC10065 by the mutant metK C94A, the metK C94A sequence from SEQ ID NO:19 was first cloned into pCLiK5MCS integrativ sacB (SEQ ID NO:12). To this end, the plasmid pCLiK5MCS/metKC94A (SEQ ID NO:19) was cleaved with the restriction endonucleases Bgl II and Xho I (NEB, Schwalbach). The resulting 1962 base pair fragment was purified as described in Example 3. The vector pCLiK5MCS integrativ sacB was likewise cleaved with Bgl II and XhoI and purified as described in Example 3. Vector and fragment were ligated and transformed into *E. coli* XL-1 Blue as described in Example 3. The plasmid was purified and, after sequencing, confirmed. The resulting plasmid pCLiK5MCS integrativ sacB/metKC94A is listed as SEQ ID NO:20.

The plasmid pCLiK5MCS integrativ sacB/metKC94A was transformed into *C. glutamicum* KFCC10065 by electroporation as described by Liebl, et al. (1989) FEMS Microbiology Letters 53:299-303. Modifications of the protocol are described in DE 10046870. The chromosomal arrangement of the metK locus of individual transformants was verified by standard methods by Southern blots and hybridization as described by Sambrook et al. (1989), Molecular Cloning. A Laboratory Manual, Cold Spring Harbor. It was thereby ensured that the transformants were those which have the transformed plasmid integrated at the metK locus by homologous recombination. After such colonies were grown overnight in media without antibiotic, these transformants were then plated onto a sucrose CM agar medium (10% sucrose) and incubated for 24 hours at 30° C.

Since the sacB gene, which is present in the vector pCLiK5MCS integrativ sacB/metKC94A, converts sucrose into a toxic product, only those colonies which have the sacB gene deleted by a second homologous recombination step between the wild-type metK gene and the mutated metKC94A gene are capable of growth. Either the wild-type gene or the mutated gene together with the sacB gene can be deleted while homologous recombination takes place. If the sacB gene together with the wild-type gene is removed, a mutant transformant results.

Growing colonies were picked out, their genomic DNA was prepared, and the metK gene was analyzed by two methods. Firstly, the substitution of two nucleotides as described in Example 4 was exploited. Diagnostic PCR fragments were generated with the aid of a specific PCR oligonucleotide primer which is capable of differentiating between the two alleles at its 3' end and a second, metK-specific oligonucleotide primer. Secondly, the metK locus of approximately 100 transformants was sequenced, after PCR amplification, with PCR oligonucleotide primers which bind upstream or downstream of the mutation. Several mutated metK clones were obtained. One such a clone was termed KFCC10065metKC94A. The amino acid sequence of mutant C94A corresponds to SEQ ID NO:22.

EXAMPLE 8

Production of Methionine using Strain KFCC10065metKC94A

The strain KFCC10065metKC94A, which had been generated in Example 6, was grown on an agar plate containing BHI medium (Difco) for 2 days at 30° C. The cells which had grown were suspended in saline from the agar plate and transferred into medium II at an OD 600 nm of 1.5. Medium II was composed as follows.

| Medium IIA | |
|---|---|
| 0.6 g/l | $KH_2PO_4$ |
| 0.4 g/l | $MgSO_4 \cdot 7H_2O$ |
| 25 g/l | $(NH_4)_2SO_4$ |
| 40 g/l | raw sugar |
| 60 g/l | molasses |

The medium prepared thus was brought to pH 7.8 with $NH_4OH$ and sterilized for 30 minutes at 120° C.

| Medium IIB: | |
|---|---|
| 0.3 mg/l | thiamine*HCl |
| 1 mg/l | biotin |
| 2 mg/l | $FeSO_4$ |
| 2 mg/l | $MnSO_4$ |
| 0.1 mg/l | vitamin B12 |

Medium IIB was prepared separately, filter-sterilized and added to medium IIA. The two components IIa and IIB together form medium II.

10 ml of medium II (=IIA+B) were treated, in a 100 ml Erlenmyer flask containing 0.5 g sterilized $CaCO_3$, with cells of the abovementioned strain and incubated for 72 hours on an orbital shaker at 30° C. at 200 rpm.

Formed methionine in the culture broth was determined with the aid of the amino acid determination method from Agilent on an Agilent 1100 Series LC System HPLC. Precolumn derivatization with ortho-phthalaldehyde permits the quantification of the amino acid formed, while the amino acid mixture is separated on a Hypersil AA column (Agilent).

We claim:

1. A method for producing L-methionine by fermentation, which comprises:
   a) fermenting a coryneform bacteria which produces L-methionine, the coryneform bacteria expressing at least one nucleotide sequence which encodes a protein with modified S-adenosyl-methionine synthase (metK) activity comprising the amino acid sequence of SEQ ID NO:22;
   b) enriching the L-methionine in the medium and/or in the bacterial cells, and
   c) isolating the L-methionine.

2. The method of claim 1, wherein said nucleotide sequence comprises SEQ ID NO:21.

3. The method of claim 1, wherein in said coryneform bacteria the metK activity is reduced in comparison with the wild type.

4. The method of claim 1, wherein the encoding metK sequence is a DNA which is capable of replication in coryneform bacteria or stably integrated into the chromosome, or an RNA.

5. The method of claim 1, wherein
   a) a bacterium which has been transformed with a plasmid vector which encodes amino acid sequence of SEQ ID NO:22 under the control of regulatory sequences is used, or
   b) a bacterium in which a nucleotide sequence, which encodes the amino acid sequence of SEQ ID NO:22 has been integrated into the bacterial chromosome is used.

6. The method of claim 1, wherein the nucleotide sequence of at least one of the genes selected from:
   a) gene lysC, which encodes an aspartate kinase,
   b) gene asd, which encodes an aspartate-semialdehyde dehydrogenase,
   c) gene gap, which encodes glycerinaldehyde-3-phosphate dehydrogenase,
   d) gene pgk, which encodes 3-phosphoglycerate kinase,
   e) gene pyc, which encodes pyruvate carboxylase,
   f) gene tpi, which encodes triose-phosphate isomerase,
   g) gene metA, which encodes homoserine O-acetyltransferase,
   h) gene metB, which encodes cystathionine-gamma synthase,
   i) gene metC, which encodes cystathionine-gamma lyase,
   j) gene metH, which encodes methionine synthase,
   k) gene glyA, which encodes serine hydroxymethyltransferase,
   i) gene metY, which encodes O-acetylhomoserine sulfhydrylase,
   m) gene metF, which encodes methylenetetrahydrofolate reductase,
   n) gene serC, which encodes phosphoserine aminotransferase,
   o) gene serB, which encodes phosphoserine phosphatase,
   p) gene cysE, which encodes serine acetyltransferase,
   q) gene cysK, which encodes cysteine synthase,
   r) gene hom, which encodes homoserine dehydrogenase, is simultaneously overexpressed, by increasing the copy number or using a strong promoter, in the coryneform bacteria.

7. The method of claim 1, wherein the nucleotide sequence of at least one of the genes selected from:
   a) gene thrB, which encodes homoserine kinase,
   b) gene ilvA, which encodes threonine dehydratase,
   c) gene thrC, which encodes threonine synthase,
   d) gene ddh, which encodes meso-diaminopimelate D dehydrogenase,
   e) gene pck, which encodes phosphoenol-pyruvate carboxykinase,
   f) gene pgi, which encodes glucose-6-phosphate-6 isomerase,
   g) gene poxB, which encodes pyruvate oxidase,
   h) gene dapA, which encodes dihydrodipicolinate synthase,
   i) gene dapB, which encodes dihydrodipicolinate reductase, or
   j) gene lysA, which encodes diaminopicolinate decarboxylase, is simultaneously attenuated, by deletion of the gene or substituting the native promoter with a weak promoter, in the coryneform bacteria.

8. The method of claim 1, wherein microorganisms of the species *Corynebacterium glutamicum* are used.

* * * * *